(12) United States Patent
Krivitski et al.

(10) Patent No.: US 7,549,965 B2
(45) Date of Patent: Jun. 23, 2009

(54) COMPENSATION METHOD FOR THERMODILUTION CATHETER HAVING AN INJECTATE INDUCED THERMAL EFFECT IN A BLOOD FLOW MEASUREMENT

(75) Inventors: Nikolai M. Krivitski, Ithaca, NY (US); Victor V. Kislukhin, Ithaca, NY (US)

(73) Assignee: Transonic Systems Inc., Ithaca, NY (US)

( * ) Notice: Subject to any disclaimer, the term of this patent is extended or adjusted under 35 U.S.C. 154(b) by 571 days.

(21) Appl. No.: 11/328,312

(22) Filed: Jan. 9, 2006

(65) Prior Publication Data
US 2006/0129053 A1 Jun. 15, 2006

Related U.S. Application Data

(62) Division of application No. 10/079,693, filed on Feb. 20, 2002, now Pat. No. 7,112,176.

(51) Int. Cl.
*A61B 5/00* (2006.01)
*A61B 5/02* (2006.01)

(52) U.S. Cl. ...................... 600/505; 600/526
(58) Field of Classification Search ................. None
See application file for complete search history.

(56) References Cited

U.S. PATENT DOCUMENTS

| | | | |
|---|---|---|---|
| 3,726,269 A | 4/1973 | Webster, Jr. | |
| 4,240,441 A * | 12/1980 | Khalil | 600/505 |
| 5,056,526 A | 10/1991 | Khalil | |
| 5,271,410 A | 12/1993 | Wolzinger et al. | |
| 5,595,181 A * | 1/1997 | Hubbard | 600/505 |
| 5,682,899 A | 11/1997 | Nashef et al. | |
| 5,833,645 A | 11/1998 | Lieber et al. | |
| 5,833,671 A | 11/1998 | Macoviak et al. | |
| 6,004,275 A | 12/1999 | Billiet | |
| 6,036,654 A | 3/2000 | Quinn et al. | |
| 6,200,301 B1 | 3/2001 | Pfeiffer et al. | |
| 6,241,667 B1 | 6/2001 | Vetter et al. | |
| 6,287,273 B1 | 9/2001 | Allers et al. | |
| 6,315,735 B1 | 11/2001 | Joeken et al. | |
| 6,355,001 B1 | 3/2002 | Quinn et al. | |
| 6,491,640 B1 * | 12/2002 | Schmalberger et al. | 600/526 |
| 6,754,608 B2 | 6/2004 | Svanerudh et al. | |
| 7,112,176 B2 | 9/2006 | Krivitski et al. | |

OTHER PUBLICATIONS

Measurement of Coronary Sinus Blood Flow by Continuous Thermodilution in Man; *Circulation*, vol. XLIV, Aug. 1971.
Measurement of Flow in Single Blood Vessels Including Cardiac Output by Local Thermodilution; Circulation Research, vol. VIII, Jan. 1960.
Measurement of Blood Flow by Local Thermal Dilution; *Society*, Mar. 20-21, 1964.

* cited by examiner

*Primary Examiner*—Robert L Nasser
(74) *Attorney, Agent, or Firm*—Brian B. Shaw, Esq.; Stephen B. Salai, Esq.; Harter Secrest & Emery LLP

(57) ABSTRACT

A catheter for retrograde orientation in a blood flow is used to determine the blood flow rate by thermodilution measurements. The determination of the blood flow rate accommodates injectate induced thermal influences on a dilution thermal sensor, wherein the thermal influences can occur prior to introduction of the injectate into the blood flow.

20 Claims, 10 Drawing Sheets $S_m = S_{dil} + S_c$

Temperature recorded by dilution thermal sensor (C)

COMPENSATION METHOD FOR THERMODILUTION CATHETER HAVING AN INJECTATE INDUCED THERMAL EFFECT IN A BLOOD FLOW MEASUREMENT

CROSS-REFERENCE TO RELATED APPLICATIONS

The present application is a division of U.S. Ser. No. 10/079,693 filed Feb. 20, 2002, entitled Compensation Method for Thermodilution Catheter having an Injectate Induced Thermal Effect in a Blood Flow Measurement and which is expressly incorporated by reference.

STATEMENT REGARDING FEDERALLY SPONSORED RESEARCH OR DEVELOPMENT

This invention was made with government support under Phase I SBIR (Small Business innovative Research Grant #1 R43 DK55444-01A2 awarded by the National Institutes of Health. The government has certain rights in the invention.

REFERENCE TO A "SEQUENCE LISTING"

Not applicable.

BACKGROUND OF THE INVENTION

1. Field of the Invention

The present invention relates to blood flow measurement by thermodilution measurement, and more particularly to compensating for an injectate induced thermal effect on a thermal sensor in a retrograde catheter.

2. Description of Related Art

In native A-V fistulae, any stenosis is often located at the arterial portion of the vascular access or A-V shunt. The existence of a stenosis in the vascular access typically requires intervention to restore sufficient flow, or at least reduce the rate of occlusion. A typical interventional procedure is angioplasty.

The purpose of the interventional procedures, such as angioplasty, is to restore the flow through the vessel. Interventional radiologists and cardiologists therefore have a need to measure the efficacy of the flow restoring procedure.

In the angioplasty procedure, an interventional radiologist will insert a sheath (introducer) for the angioplasty balloon catheter facing the stenosis location and thus facing the blood flow in the vessel such as an A-V shunt. It is procedurally convenient to use the same introducer (sheath) for flow measurement. This procedure will locate the thermodilution catheter facing the blood flow and the position, facing the flow, is termed as "retrograde" position. Also in clinical situations such as angioplasty of extremities, it is convenient to reach the stenosis location from a downstream cannulation site. In all these situations, the thermodilution catheter will be facing the flow, and thus in a retrograde position. Yet, there remains a need for determining the blood flow rate.

Another situation is related to the endovascular procedure of placement of transjugular intrahepatic portosystemic shunts (TIPS). During the TIPS procedure, a special shunt is created to connect the portal vein with hepatic vein. The TIPS procedure is usually done to decrease the portal hypertension. However, the amount of blood that is taken by the shunt is unknown. If the amount of blood flow through the shunt is too high, then the amount of blood passing through the liver to be filtered is too small, which can result in damage to the patient. Alternatively, if the amount of blood flowing through the shunt and thus shunted from the liver, is small, then the effectiveness of the procedure is diminished. The need exists for determining the blood flow so that proper treatment can be administered.

Currently, blood flow measurements are performed not during intervention but later using color Doppler measurements of line velocity, but do not provide a blood flow measurement in ml/min.

Not withstanding, no practical, relatively quick, and low cost solution exists in the prior art for determining the relevant flow in these example procedures. Therefore, the need exists to measure blood flow using a catheter introduced into the vessel in retrograde direction. It is an object of the present invention to provide low cost flow measurement methods and devices for such measurements which solve the problems (and design constrains) of the retrograde thermodilution catheter.

BRIEF SUMMARY OF THE INVENTION

The present invention is generally directed to determining blood flow rates, and more particularly to indicator dilution techniques, wherein a signal is introduced into the blood upstream and a downstream dilution signal is sensed. Of the indicator dilution methods, thermodilution is applicable in the present disclosure. In thermodilution measurements, an injectate (having a different temperature than the blood flow to be determined) is introduced at an upstream location and a thermal sensor (or dilution thermal sensor) monitors passage of the injectate at a downstream location.

In a number of configurations, a thermodilution catheter is employed, wherein the catheter includes an injectate lumen for introducing the injectate into the relevant blood stream and a dilution thermal sensor for monitoring a downstream passage of the injectate in the blood stream. The catheter can also include an injectate thermal sensor for providing a signal corresponding to an injectate temperature prior to introduction of the injectate into the blood flow.

As a consequence of thermal transfer, such as conduction or radiation within the catheter, the dilution thermal sensor in the retrograde catheter will register temperature changes, or effects, both by the injectate (indicator) passing through the catheter and the diluted blood flowing past the catheter. In this case, inside cooling of the dilution thermal sensor falsely increases the area under the resulting dilution curve and thus decreases the accuracy of the measurement.

The present invention also provides for measurement of the blood flow during the TIPS procedure, wherein the measurements can be conveniently performed by a retrograde catheter, introduced for example through the jugular vein, through the vena cava, and through the hepatic vein.

The measurements can be performed before intervention, after the shunt construction, in the shunt and in the vena porto (portacaval shunt). In this case, the retrograde catheter can be introduced through the hepatic vein, through the shunt and into the vena porta. The advantage of a blood flow measurement during the intervention is the ability to change the shunt flow if the shunt flow is not adequate.

The present configurations are directed to improving blood flow measurement accuracy in thermodilution measurements in a retrograde catheter by accounting for the presence of the inside cooling effect. The present configurations include (i) the pre-calibration of the thermal conductive properties of the catheter to determine $K_i$ over an intended range of operating conditions, wherein the calibration data is used to adjust thermal measurements; (ii) a plurality of injections of different volumes or different time length from which a cooling effect on the dilution thermal sensor from inside the catheter can be determined, and/or an injectate temperature can be calculated; (iii) a plurality of thermal sensors, where the magnitude of the inside cooling effect on the dilution thermal sensor is measured by an additional thermal sensor and compensated; (iv) a plurality of pre-calibrated thermal sensors, to simultaneously eliminate the necessity of measuring the injectate temperature and the inside cooling effect; (v) creating special construction of the retrograde catheter to enhance, or maximize the thermal isolation of the injectate lumen from the dilution thermal sensor; or (vi) employing any combination of i-v.

BRIEF DESCRIPTION OF THE SEVERAL VIEWS OF THE DRAWING(S)

FIG. 13b is a cross sectional view taken along lines 13b-13b of FIG. 13a.

FIG. 14b is a cross sectional view taken along lines 14b-14b of FIG. 14a.

FIG. 15b is a cross sectional view taken along lines 15b-15b of FIG. 15a.

DETAILED DESCRIPTION OF THE INVENTION

Figure 1:
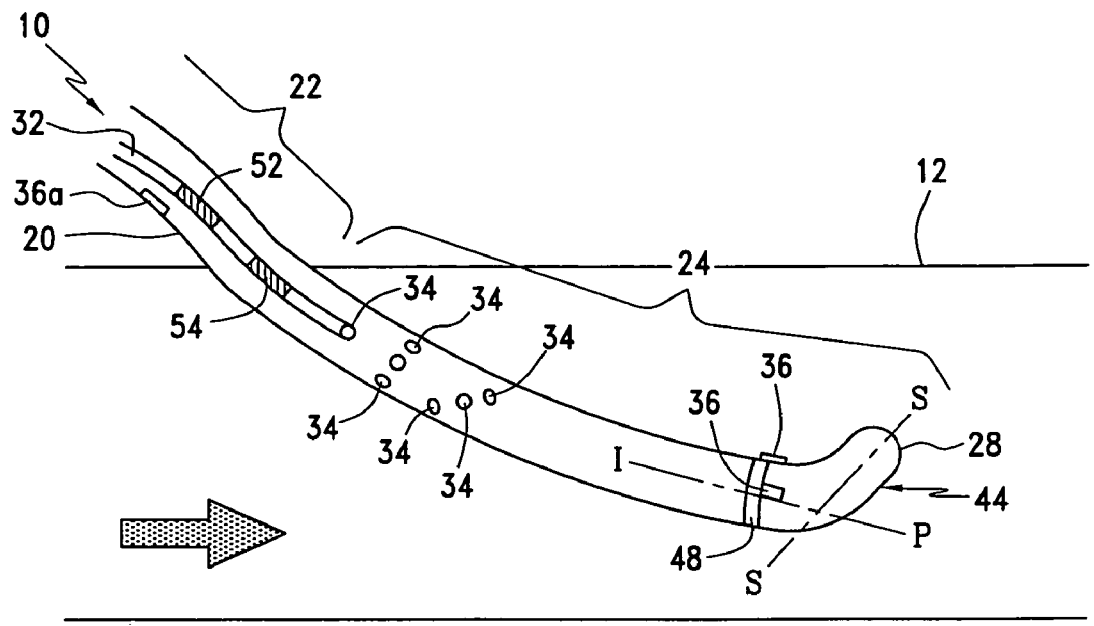
FIG. 1 is a cross sectional view of an indicator dilution catheter inserted in a vessel in the downstream direction of the blood flow and curved to reduce sensor contact with the vessel wall.
Figure 2:
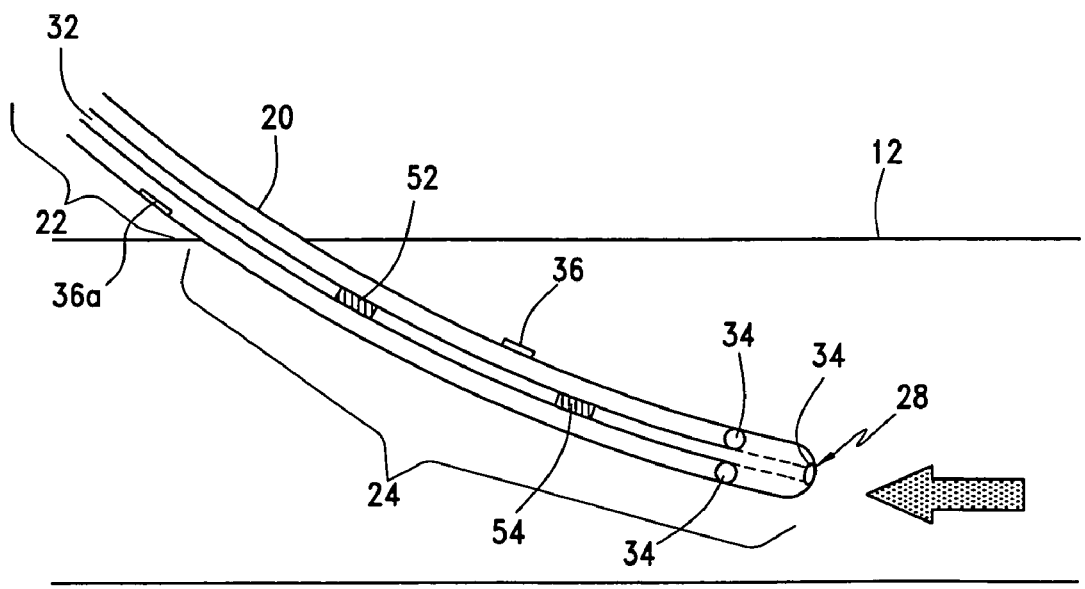
FIG. 2 is a cross sectional view of an indicator dilution catheter inserted in the vessel in the upstream direction, thus facing the blood flow.

Referring to FIGS. 1 and 2, the present indicator dilution catheter 10 is shown operably located in an arterio-venous (A-V) shunt 12. The A-V shunt 12 has a blood flow shown by the direction of the arrows, the catheter 10 includes an elongate body 20 having an extravascular portion 22 and an intravascular portion 24. The extravascular portion 22 being that portion or length of the body 20 that is not operably located within the A-V shunt 12 to contact the blood flow in the shunt. The intravascular portion 24 is that portion or length of the body 20 that is operably located within the A-V shunt 12 and contacts the blood flow in the shunt. The body 20 includes a proximal end, a distal end 28, an indicator (injectate) lumen 32, an injection port(s) 34 and a dilution sensor 36 for detecting passage of the injected indicator in the blood flow in the A-V shunt 12. That is, the dilution sensor measures a temperature of the diluted blood flow resulting from introduction of the injectate into the blood flow. Typically, the catheter 10 is operably connected to, or connectable to a controller. The controller can be a dedicated unit including hardware and software.

In operation, the indicator passes along the catheter 10 through the injectate lumen 32 to be introduced into the A-V shunt 12 blood flow through the injection port 34. The dilution sensor 36 is typically connected to the controller via a lead or wire extending along the catheter 10.

It is important for the dilution sensor 36 inside the blood stream to avoid contact with the A-V shunt wall or influence of the A-V shunt wall. To reduce the likelihood of the dilution sensor 36 touching the wall, a special curvature of the catheter 10 as seen in FIG. 1 can be used. This curvature is selected to reduce the potential for contact between the dilution sensor 36 and the A-V shunt wall. A length of the intravascular portion 24 of the body 20, and typically a length proximal to the distal end 28 of the body includes an inclined spacing section 44. The spacing section 44 has a longitudinal axis S-S that is non co-linear and non parallel to the longitudinal axis IP of an adjacent section of the intravascular portion 24. That is, the longitudinal axis of the spacing section 44 intersects the longitudinal axis of the adjacent section of the intravascular portion 24.

As the preferred configuration of the catheter 10 is directed to thermodilution, the dilution sensor 36 is a thermal sensor such as a thermistor. Preferably, the dilution sensor 36 has as small a volume as possible, so that the cross sectional area of the catheter 10 can be effectively minimized. However, it is understood the thermal sensor 36 can be any sensor that can measure temperature, for example, but not limited to thermistor, thermocouple, electrical impedance sensor (electrical impedance of blood changes with temperature change), ultrasound velocity sensor (blood ultrasound velocity changes with temperature), blood density sensor and analogous devices. In fact, any parameter of blood that changes with temperature can be used to obtain thermodilution measurements.

However, the present invention is particularly applicable to those thermal sensors having a performance that is temperature dependence. That is, those sensors that are effected by induced temperature fluctuations from exposure to a cooled or heated injectate (indicator) passing through the catheter. Temperature sensors are suited to the present invention, as the temperature of the sensor (and hence recorded temperature) can be effected by cooling or heating from the injectate prior to introduction of the injectate into the flow to be measured.

The dilution sensors 36 detect a blood parameter and particularly variations of a blood parameter. For example, the dilution sensors 36 may be electrical impedance sensors, or optical sensors, the particular sensors being dependent on the blood characteristics of interest. Ultrasound velocity sensors, as well as temperature sensors and optical density, density or electrical impedance sensors can be used to detect changes in blood parameters. The operating parameters of the particular system will substantially dictate the specific design characteristics of the dilution sensor 36, such as the particular sound velocity sensor. If a plurality of dilution sensors 36 is employed, the sensors can be identical components. Ultrasonic sensors measure sound velocity dilution as the indicator material is carried past the sensor by the bloodstream, and changes in sound velocity are plotted to permit calculation of various blood parameters. The time at which the indicator material (injectate) reaches the sensor 36 after injection, the area under the plotted curve representing the changes in sound velocity at the sensor, and the amplitude of the measurement all provide information concerning the blood flow.

The indicator includes, but is not limited to any of the known indicators including a temperature gradient indicator, such as a bolus of a continuous injection.

Preferably, the indicator is injectable through the injection port 34 and is thus an injectate. The injected (or introduced) indicator, injectate, thus forms an indicator bolus.

The injected indicator, a liquid, can be a solution that is preferably non detrimental or minimizes any detriment to the patient, the blood of the patient, any blood components, including blood, and is non-reactive with the material of the system, including the material of A-V shunt. A preferred indicator is a solution such as isotonic saline and dextrose (glucose). However, it is understood any of a variety of solutions can be employed. Further, the term solution is taken to include single component injections. For thermodilution measurements, the injectate has a different temperature than the blood flow into which the injectate is introduced.

The present analysis is set forth in terms of a reduced temperature indicator, such as an injectate. That is, the indicator has a temperature below the temperature of the blood flow to be measured. However, it is understood that an elevated temperature indicator can be employed. That is, a temperature that is above the temperature of the blood flow to be measured.

The present invention provides for the determination of a volumetric flow rate ("flow rate") in an A-V shunt 12. The volumetric flow rate is a measure of the volume of liquid passing a cross-sectional area of the conduit per unit time, and may be expressed in units such as milliliters per min (ml/min) or liters per minute (l/min). A liquid flow having a flow rate also has a flow velocity, the distance traveled in a given time, such as millimeters per second (mm/s). Thus, for liquid flowing in an A-V shunt, there will be a flow rate (volumetric flow rate) having a flow velocity.

Blood flow rate (Q) can measured by thermodilution, using an indicator having a different temperature than the blood (typically through an injection of a liquid indicator (injectate)), wherein the blood flow rate Q can be presented by the following formula:

$$Q = k(T_b - T_i)\frac{V}{S} \qquad \text{(Equation 1)}$$

where $T_b$ is blood temperature in the vessel prior to injection; $T_i$ is the temperature of the injectate prior to it entering the blood stream; V [ml] is the volume of injected indicator (injectate); S [temp*time] is the area under the temperature versus time dilution curve resulting from the mixing of the injected indicator (injectate) and the blood; and k is a coefficient related to thermal capacity of blood and the injected indicator (injectate). Typically, k is taken to be 1.08.

For continuous injections in Equation 1, V [ml/time] is the speed (rate) of the continuous injection, S [temp] is the temperature change of the blood due to mixing with the indicator, wherein the indicator can be colder/warmer than the blood.

A major difference between the classic dilution measurements of cardiac output and the measurements of blood flow rate in A-V shunts 12, wherein the indicator is introduced and a corresponding measurement is taken within a given section of the A-V shunt, is the absence of a mixing chamber such as the heart. That is, in classic dilution measurements of cardiac output, the blood and the indicator flow through the heart, which sufficiently mixes the indicator (thermal change) with the blood to provide reliable measurements.

However, if the blood and the indicator do not travel through a mixing chamber such as the heart, the design of the measurement system must provide for adequate mixing of the indicator with the blood within the space between the indicator introduction (injection) and the site of resulting dilution measurement.

The adequacy of mixing can be judged by comparing results of the dilution measurement with a more accurate method like, for example, volumetric timed collection of flow on the bench. If other sources of errors are controlled, the discrepancy between the measurement results can be attributed to inadequate mixing conditions.

Whether the mixing is adequate depends on the requirements of the clinical users and the dynamic range of the measured parameters. For example, for an angioplasty restoring procedure in A-V lower arm shunts, an average increase of the blood flow after angioplasty procedure is approximately 300-400 ml/min from 400-600 ml/min to 700-1000 ml/min. A measurement method would reliably indicate such procedural changes in flow, if its absolute error of flow measurement is less than the larger of 60-100 ml/min or 10%.

There are two different orientations for catheter placement in the A-V shunt 12. The A-V shunt 12 normally has a single flow direction, wherein blood flows from the arterial (upstream) side to the venous (downstream) side. Thus, the term downstream indicates directed with the flow, and the term upstream indicates directed against the flow.

1. Referring to FIG. 1, a catheter 10 is placed in the direction of blood flow, pointing downstream. In this case, the injected indicator enters the blood flow from a point along the catheter 10, or upstream of the catheter, and the dilution temperature change can be recorded by the dilution sensor 36 at or near the distal end 28 of the catheter 10.

2. Referring to FIG. 2, the catheter 10 is placed facing the blood flow, pointing upstream (the retrograde position or configuration). In this case, if the injected indicator is introduced in the blood flow of the A-V shunt via the same catheter, the indicator will first travel past the dilution sensor 36 as the indicator passes along the indicator lumen 32.

To enhance the accuracy of the measurements of blood flow rates using thermodilution, the following problems associated with specifics of thermodilution blood flow measurement within the A-V shunt 12 should be addressed:

(i) Supporting mixing conditions; and (ii) Reducing measurement errors resulting from the introduction of an indicator.

(i) Supporting Mixing Conditions

Various mechanisms can be implemented for enhancing the mixing conditions within the A-V shunt 12:

(a) Plurality of injection sites To create a uniform indicator distribution throughout the cross section of the flow in the A-V shunt 12, a plurality (two or more) of injection ports 34 for indicator introduction can be used. These injection ports 34 can be located on the same level or at different levels within, or across the cross sectional profile of the A-V shunt. These injection ports 34 can be located to face the flow, be with the flow or have spiral form or other forms, locations and configurations. It is preferable that the indicator pass through the catheter 10 in a single lumen or channel 32, from which the indicator is distributed to the plurality of injection ports 34. FIG. 1 depicts multiple configurations of arrays for the injection ports 34. It is understood a single array of injection ports would be employed in a catheter, and the multiple arrays in FIG. 1 are for illustration purposes. In FIG. 2, two locations of the injection port 34 (single port or in array form) are shown, again with the understanding a single configuration is employed in a given catheter 10. Specifically, the injection port 34 can be at the distal end 28 or proximal to the distal end.

(b) Plurality of dilution sensors to increase the accuracy of the measurements, especially in conditions where desired mixing may be difficult to achieve, a plurality of dilution thermal sensors 36 can be used. The plurality of dilution thermal sensors 36 are particularly applicable in conjunction with catheters having one port, a plurality ports, or a non volume indicator introduction such as the heating or cooling of the blood. In addition, a plurality of dilution sensors 36 can be employed when the indicator is introduced through a separate introducer, rather than the catheter on which the dilution sensors are located. Further, corresponding to the graph of FIG. 5 and seen in FIGS. 1 and 2, a sensor 36a can be located outside the A-V shunt 12 to provide the measurement of the passage of the indicator through the shunt. The flow rate $Q_c$ may be calculated from the individual dilution sensor measurement Q1, Q2, Q3, . . . for example, as follows. If the sensors are disposed, about a circle or ring, simple averaging can be performed:

$$Q_c = \frac{(Q_1 + Q_2 + Q_3 + \ldots Q_n)}{n} \qquad \text{(Equation 2)}$$

where n is the number of sensors. Alternatively, the area under the dilution curve associated with each sensor can be summed and averaged for determining the flow. As a further refinement, one could evaluate all individual sensor readings and discard one if its measurement indicates that the sensor is positioned against the vessel wall.

(c) Turbulent introduction of the indicator into the blood flow in the A-V shunt. The kinetic energy introduced into the initial blood flow Q by the injected indicator can enhance the mixing conditions by creating turbulence in the blood flow. This can be achieved by making the opening(s) 34 in the catheter 10 from where the indicator leaves the catheter and enters the blood stream sufficiently small so the indicator will "jet" into the flow at a higher velocity than the present blood velocity. The turbulence may be enhanced by angling these holes so the injection jet is directed against the direction of blood flow in the A-V shunt 12. The turbulence may be enhanced by the use of a plurality of holes spaced around the perimeter of the catheter, such as along a ring. However, for the jetting introduction, the injection ports 34 are sized to at least substantially preclude hemolysis in the A-V shunt 12.

(d) Use of a thermally conductive band. Placing a thermally conductive band 48 around the catheter at the site of the indicator dilution sensor 36 and in close thermal contact with the sensor. Such a band, typically constructed of metal, will assure that the dilution sensor 36 will average the temperatures of a larger cross sectional area of the blood flow, and will thus partly offset variations in blood temperature that result from inadequate mixing. As the sensing will be done around the full perimeter of the catheter 10, such a band 48 will also reduce the loss in measurement accuracy that results when an un-banded indicator dilution sensor is positioned against the wall of the A-V shunt 12.

The distance between the injection port 34 and the dilution thermal sensor 36 are preferably selected to provide sufficient mixing of the introduced indicator and the blood. For the catheter 10 facing the flow, the distance between the port 34 and the sensor 36 is approximately 2 to 4 cm. For the catheter 10 oriented with the flow, the distance between the injection port 34 and the sensor 36 is approximately 3 to 6 cm.

(ii) Reduce Measurement Errors Resulting from the Introduction of an Indicator.

The introduction of a volume of indicator at a flow rate $Q_i$ can change the initial flow rate Q. The effect of $Q_i$ depends on the particulars of the hemodynamic resistance of the A-V shunt 12.

In the arterial environments, the major resistance to flow is downstream where the downstream resistance may well exceed the upstream resistance 20-100-fold. Thus, the injected flow does not change the initial flow at the site of the sensor. During the injection period, the arterial inflow into the measurement site will temporarily reduce in response to the introduced injection. In this case, the recorded dilution curve will represent the initial blood flow rate, and the measured blood flow rate $Q_m$ will be close to initial blood flow:

$$Q_m = Q \qquad \text{(Equation 3)}$$

In the venous environments, the main flow resistance is upstream from the measuring site, where the flow resistance may exceed the downstream flow resistance 20-100-fold. In this situation, the dilution measurement $Q_m$ will represent the sum of initial flow and injected flow:

$$Q_m = Q + Q_i. \quad \text{(Equation 4)}$$

In A-V shunt systems 12 the location and distribution of the resistances is unknown. That is, the resistance to flow can be downstream in which the volume of the introduced indicator will effectively not be seen. Alternatively, the resistance to the flow in the A-V shunt 12 can be upstream, in which case the measured flow will include at least a portion of the flow rate of the introduced indicator. In the A-V shunt 12, the flow resistances will depend on factors such as initial surgical anatomical construction of the shunt, locations of stenoses and placement of the catheter. Thus, contrary to the arterial and venous environment, the relationship of the measured flow rate $Q_m$ in A-V shunts to initial blood flow rate is unknown. The measured flow rate $Q_m$ will be somewhere between initial flow Q and the initial flow plus injection flow $Q+Q_i$, depending on distribution of resistances in relation to the place of the injection. The range of uncertainty directly depends on the injection flow rate $Q_i$. Therefore, while a larger $Q_i$ is desirable for enhancing mixing conditions, the relatively large $Q_i$ may result in a less accurate flow measurement because of the unknown effect of $Q_i$ on the initial flow rate. The best flow rate $Q_i$ is a compromise: not too large, not too small. To minimize the error from the injection flow rate $Q_i$ being too large or too small, the following can be employed:

1. Calculating the flow rate $Q_c$ based on the injection flow rate $Q_i$ and on information of measurement conditions such as the type of the A-V shunt, the distribution of the resistances and the value of $Q_m$ itself.

2. Limiting the ability of operator to inject the indicator too quickly, while still providing sufficient ejection velocity to enhance mixing.

3. Rejecting the result of the flow measurement $Q_m$, if the flow rate of the injection $Q_i$ is too high or too low.

4. Employing two injection flow rates to gain a further improvement in shunt flow measurement accuracy and to reveal the location of the hemodynamically significant stenosis in the A-V shunt.

1. Calculating $Q_c$ by Adjustment of the Measured Value of $Q_m$

In high-flow, well developed native fistula, the major flow resistance (between 50% and 100%) is located at the arterial anastomosis. This means that the flow resistance downstream from the injection is between 0 and 50% of the total flow resistance. For this case the flow measurement error is reduced by using a flow calculation algorithm, which places 75% of the flow resistance upstream from the point of indicator introduction, 25% downstream. The calculated flow $Q_c$ will then be $$Q_c = Q_m - 0.75 Q_i \quad \text{(Equation 5)}$$

In this case the possible error introduced by the injection flow will be less than 25% of $Q_i$.

In most well functioning lower arm artificial grafts, blood flow is in the range of 1000-1600 ml/min. The literature suggests again that the major flow resistance (between 50% and 100%) is located upstream from the catheter (arterial anastomosis, supplying artery). Therefore, equation 5 can be used.

Therefore, if the indicator dilution measurement of shunt flow is 1100-1200 ml/min or more the flow measurement device or controller may be configured to automatically use Equation 5.

On the other hand, flow limiting stenoses in artificial grafts generally develop in the venous outflow side of the A-V shunt. Therefore, if the angiogram reveals that such is the case, another measurement algorithm for such specific instances can be used. Assuming that at least 50% of the flow resistance is now on the venous side, the algorithm could now be:

$$Q_c = Q_m - 0.25 Q_i \quad \text{(Equation 6)}$$

In this case the possible error introduced by the injection flow will again be less than 25% of $Q_i$.

In the general case when the distribution of hemodynamic resistances is unknown, one may minimize influence of injection flow on the flow reading reported to the operator through the use the following equation to calculate initial flow $Q_c$:

$$Q = Q_m - \frac{Q_i}{2} \quad \text{(Equation 7)}$$

In this case the error from the injected flow will be less than 50% of $Q_i$.

Figure 4:
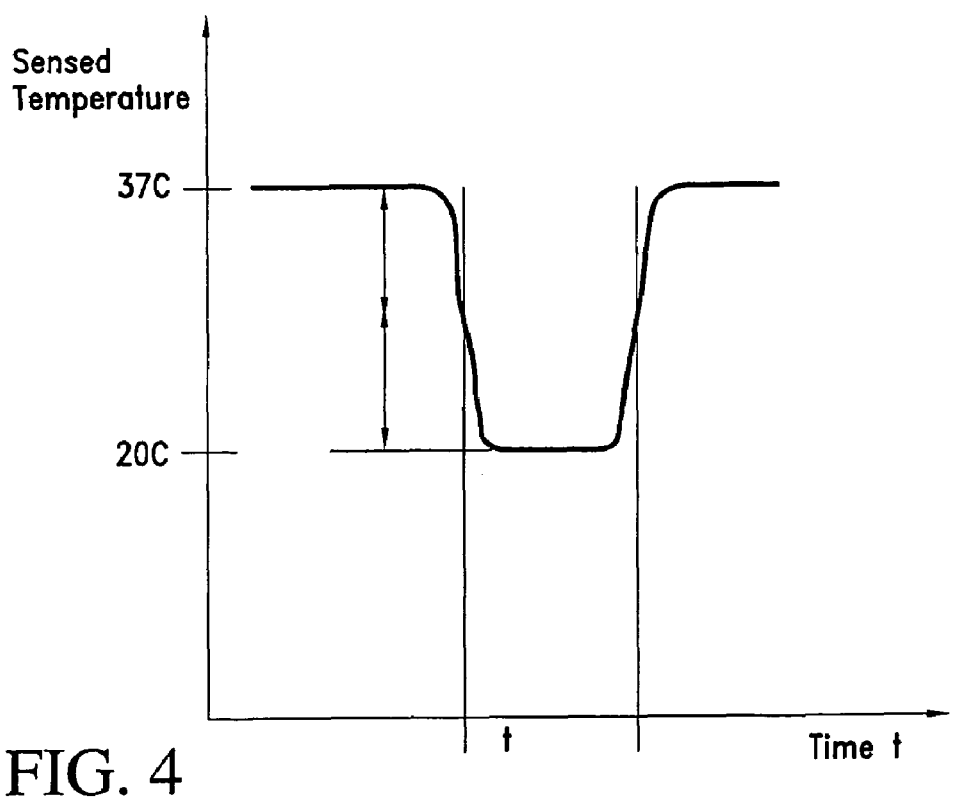
FIG. 4 is a graphical representation of the relationship between time and temperature by the injection temperature sensor and measurement of injection time, when such injection temperature sensor is located in a portion of the catheter in contact with the blood stream.
Figure 5:
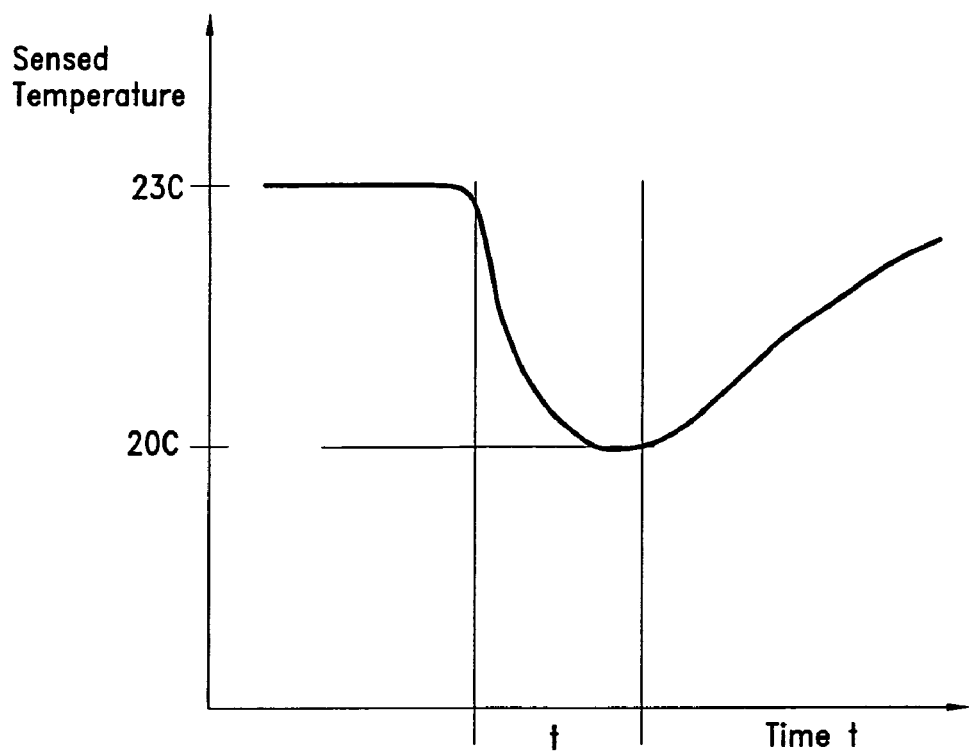
FIG. 5 is a graphical representation of the relationship between time and temperature by the injection temperature sensor and measurement of injection time, when such injection temperature sensor is located outside the blood stream and the body of the patient.

The value of $Q_i$ can be estimated, for example, as a ratio of known injected indicator volume (V) and time of injection (t):

$$Q_i = \frac{V}{t} \quad \text{(Equation 8)}$$

wherein the time of injection t can be estimated from the temperature curve of a thermal sensor. For example, the time t can be derived from the indicator dilution curve, from the width of that curve at its half height (FIG. 3), or from the time period between the beginning the bolus registration to the moment to the beginning of the downslope. Alternately, the time t can be derived from the curve from the injection thermal sensor by the time period between the beginning of the bolus to the beginning of the downslope (FIG. 4 and FIG. 5). Alternatively, if a dedicated indicator injection pump is used, the value of the injection time can be acquired from the pump setting.

2. Limiting the Ability of the Operator to Introduce the Indicator Too Quickly

In practice, it is important to limit the ability of the operator to inject the indicator too quickly, thus introducing large flow changes. For example, in [Ganz 1964] the authors injected 5 ml of saline in 0.3-0.5 second, which results in an injected flow rate of Qi=600-1000 ml/min. This injected flow rate is unacceptable in A-V shunt flow measurements because the injected flow rate may exceed the actual flow in the shunt, thereby introducing large error. Thus, the speed of the indicator injection is a compromise between the need to achieve sufficient mixing (the higher injection flow the better chance of sufficient mixing) and the need to limit the flow rate of the indicator injection because of increase in error due to unknown distribution of resistances.

To limit the ability to inject too quickly, the indicator lumen 32 and/or injection port(s) 34 can be designed to be sufficiently small to increase the resistance to flow. That is, flow resistance of the indicator through the indicator lumen or the injection ports is selected to limit the injection rate.

For example the indicator lumen or the flow path of the indicator can include a tortuous flow path 52 which provides sufficient resistance to flow to preclude a injection flow rate greater than 200 ml/min. In a preferred configuration, the injection rate is between approximately 60 ml/min to 200 ml/min. The resistance is selected to provide the desired flow rate for, or within, normal anticipated pressures on the indicator. Also, the indicator may pass through a cellular structure 54 to create the desired flow resistance. It is also contemplated the injection port(s) 34 can be sized to create at least a portion of the flow resistance to limit the upper end of the indicator injection flow rate. In a preferred embodiment, the injection ports 34 of the catheter 10 may be dimensioned to serve this function.

As an alternate, flow-limitations may be programmed into an automated pump that provides controlled indicator injections. This pump can be programmed to repeat measurements if the pump rate is improper based on the measured rate of shunt flow, and repeat such measurements at a more optimal rate of pump flow.

3. Rejecting the Result of the Flow Measurement If the Injection Flow Rate is Too High or Too Small The rejection of the flow measurement if the introduced indicator flow rate is too small or too large can be accomplished by the controller operably connected to the sensor 36. The controller can include software for determining the length of time of the indicator injection and subsequently reject the measured flow rate, if the indicator flow rate was too great or too small. The controller can be configured to estimate an indicator injection rate, or rely upon an absolute time t of the injection. For example, if the 10 ml injection time t is less than 2 seconds (Qi>300 ml/min), the controller can reject the resulting measured flow rate. Further, if the if the injection time t is greater than 10 seconds (Qi<60 ml/min), the controller can reject the resulting measurement as the desired mixing may not have been achieved. Such controller may be structured to provide error warnings to the operator.

The window of injection times accepted by the controller can be selected to automatically take into account the A-V shunt flow reading. For instance, if the indicator dilution reading would be 2000 ml/min, an injection flow rate of 300 ml/min may still be acceptable. If the indicator dilution reading would be only 400 ml/min, the same 300 ml/min injection rate could create unacceptable measurement tolerances and an operator warning could be issued to redo the measurement at a slower injection rate.

4. Employing Two Injection Flow Rates.

Two successive indicator dilution measurements performed at different injection flow rates can be made to further increase the A-V shunt flow measurement accuracy and/or gain knowledge on whether the flow limiting stenosis in the shunt is located on the arterial or on the venous side of the shunt.

Analogous to equations 5-8, two injections with different injection flow rate $Q_{i1}$ and $Q_{i2}$ will produce two measured flow rates $Q_{m1}$ and $Q_{m2}$:

$$Q = Q_{m1} - pQ_{i1} \quad \text{(Equation 9)}$$

$$Q = Q_{m2} - pQ_{i2} \quad \text{(Equation 10)}$$

where p is the portion of injection flow that adds to the initial flow and should be subtracted from measured flow.

Equations 9 and 10 can be solved for the two unknowns p and the initial shunt flow Q:

$$Q = \frac{(Q_{m1} \times Q_{i2} - Q_{m2} \times Q_{i1})}{(Q_{i2} - Q_{i1})} \quad \text{(Equation 11)}$$

$$p = \frac{(Q_{m1} - Q_{m2})}{(Q_{i1} - Q_{i2})} \quad \text{(Equation 12)}$$

For accurate measurement of p and Q using Equations 11 and 12, the difference between the two injection rates, ($Q_{i2} - Q_{i1}$), should be as large as possible. That is, if $Q_{i2}$ and $Q_{i1}$ approach each other, the numerator becomes too large and thus introduces an unacceptable amount of error into the calculation.

Both indicator introductions, or one of them may be performed from the same catheter where dilution sensor(s) is (are) located, or through another catheter or through the introducer, or through a needle. Injections of different rates also can be done by the dedicated pump. In one embodiment, a slow injection can be performed through the catheter where flow is restricted, a quick injection can be performed through the introducer of this catheter (the "sheath"). One may also use a catheter with two separate channels (lumens) with different resistances for injection at different flow rate. Alternatively, one can use a catheter with one injection lumen, where the injection into this lumen takes place via a flow restricting valve with at least two positions.

In instances where it is impractical to inject at two flow rates that are sufficiently different to yield accurate values for Q and p in Equations 11 and 12, the two-injection method can still be used to eliminate some of the influence of the injection flow rate on the measurement and thus improve measurement accuracy. In this instance, one would only employ Equation 12 to find a rough estimation of the value p. If p is well below 50% one can conclude that the main flow resistance is located in the shunt downstream from the injection port(s). Therefore, the use of Equation 6 is indicated to calculate shunt flow $Q_c$; one should then calculate $Q_c$ using the indicator dilution measurement done at the lower injection flow rate. Conversely, if p is found to be substantially larger than 50%, the main flow resistance is likely located in the shunt upstream from the injection port(s). In this instance the use of Equation 5 is indicated for calculating $Q_c$ (again using the indicator dilution measurement made at the lower injection flow rate). If p is found to be near 50%, an intermediate injection flow correction ($Q_c = Q_m - 0.5Q_i$) is appropriately used. In all these instances, the error introduced into the measurement of Q stemming from the injection flow is reduced to 25% of the injection flow.

The measurement of p in the above approach yields further information, helping the radiologist to select appropriate corrective procedures. As disclosed above, the value of p reveals whether the flow limiting stenosis is located upstream or downstream from the catheter's flow measurement site. It therefore informs the radiologist at which side of the shuns he/she should perform the flow-restoring procedure. At a small value of p and low shunt flow, the hemodynamically significant stenosis is located at the venous side of the shunt; for a large value of p and small shunt flow it is located at the arterial end.

Although the family of inventions disclosed herein is primarily described on the basis of a thermodilution catheter, the spirit of invention and equations 2-12 can be used for any dilution catheter. Further, the application need not be limited only to A-V shunts, but can be employed in any vessel, conduit or channel, where the amount of flow resistance and/or the location of the flow resistance in the flow path (relative to the injection site) is unknown. The flow measurement $Q_m$ can be made using any indicator dilution method without departing from the spirit of this invention. Measurement or determination of the injection flow $Q_i$ can be calculated from any dilution curve like (FIG. 3); from the measurement the signal of an injection sensor; from a dedicated indicator injection pump setting, or simply by dividing the volume of indicator as indicated on the injection syringe by the injection time as measured by stopwatch, or any other method know in the art. The calculated flow $Q_c$ can be determined from a flow measured by any method known in the art, and the exact correction factor used for $Q_i$ in such a calculation can vary between 0 to 100% using without departing from the spirit of this invention. That is, $Q_m$ can be determined by any methodology, formula or derivation, whereupon the present invention of determining $Q_c$ can be performed by modifying the measured flow $Q_m$. It is also understood the dilution measurements can be made percutaneous. That is, the sensors 36a can be located outside of the vessel or shunt 12 to measure the indicator in the flow within the shunt, wherein the resulting measured flow can be modified by the present formulas and concepts. Thus, the sensors 36, 36a can be optical, electrical, impedance, ultrasound or other sensor that can provide measurements of the indicator within the shunt 12 percutaneously.

When the thermodilution measurements are performed with the catheter facing the blood flow (in the retrograde position), as seen in FIG. 2, the injected indicator (injectate) will cool the dilution thermal sensor 36 through the catheter walls while passing within the catheter to the distal part (tip part) of the catheter 10. Thus, when the diluted cooled blood contacts the dilution thermal sensor 36, the dilution thermal sensor will already be cooled to some degree by the internal passage of the indicator, and the signal from the thermal dilution sensor will be thus influenced by both the cooling energy from the inside the catheter 10 and the cooling energy from the diluted outside blood flow (the blood flow in the vessel). The dilution sensor is that sensor which senses the temperature of the diluted blood flow in the conduit.

Figure 6:
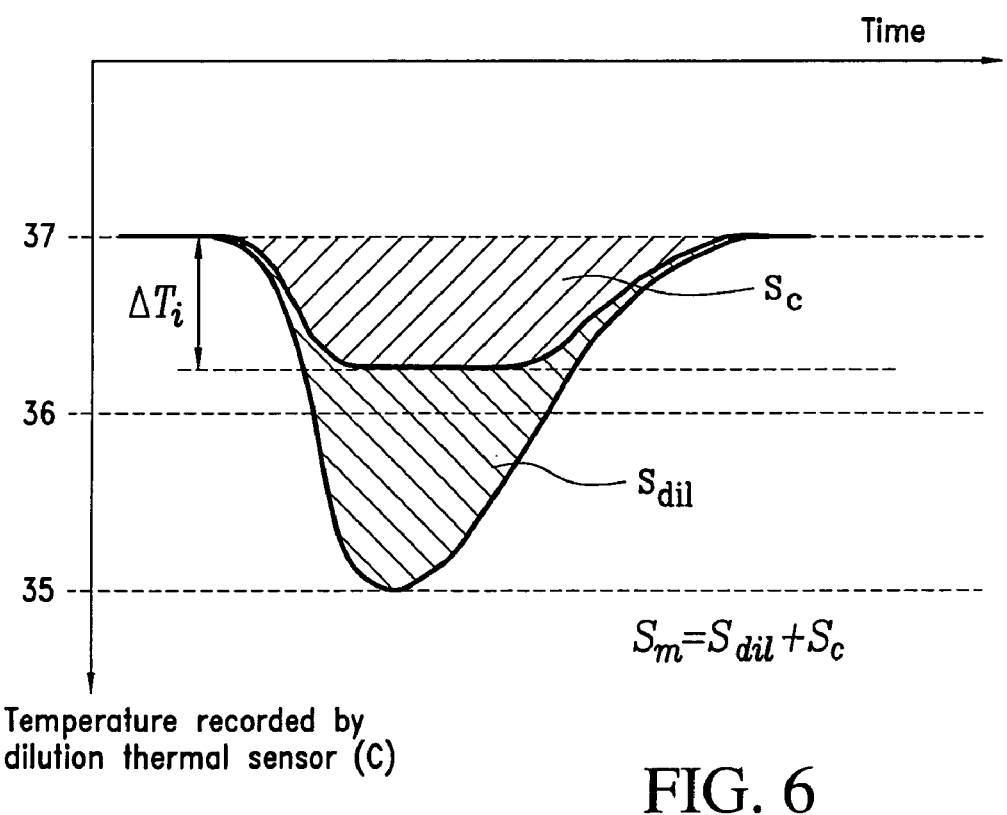
FIG. 6 is a graphical representation of a thermodilution curve from the catheter inserted facing the direction of blood flow (retrograde).

The cooling of the dilution thermal sensor resulting from the indicator (injectate) flowing through the injection (injectate) lumen 32 will hereafter sometimes be referred to as the "inside cooling" and the "inside cooling effect". The inside cooling effect can introduce a significant error by a spurious increase in the area under dilution curve seen in the blood flow measurement (FIG. 6 area $S_c$).

The injectate thus creates a measurement (or signal) offset in the dilution sensor. That is, the dilution sensor would provide a different measurement or signal in the absence of the injectate travelling through the catheter (prior to introduction) into the blood stream. Typically, this measurement offset is a change in the temperature of the dilution sensor resulting from thermal exposure of the dilution sensor to the injectate in the catheter.

The blood flow rate ($Q_f$) measured by the retrograde thermodilution catheter (facing the blood flow) will be:

$$Q_f = \frac{kV(T_b - T_i)}{(S_m - S_c)} - Q_i^* \qquad \text{(Equation 13)}$$

where $S_m$—is the total area under dilution curve; $S_c$—is the portion of the area under dilution curve related to the inside cooling effect, $Q_i^*$ adjustments for injection flow $Q_i$. The $Q_i^*$ correction term may be omitted in cases where it is a negligible portion of $Q_f$ and this term is not entered in later equations derived here from Equation 13. Nevertheless, those later equations should be read to include the $Q_i^*$ correction term in cases where added measurement accuracy is desired.

The theory and the experiments show that the inside cooling effect that produces the temperature change $\Delta T_i$ of the dilution sensor 36 (see also area $S_c$ FIG. 6) can be conveniently characterized through a thermal transfer coefficient $K_i$. The thermal transfer coefficient $K_i$ characterizes the relationship of the measured temperature difference between the blood and the injectate (injected indicator) and the temperature change $\Delta T_i$ of the dilution sensor:

$$\Delta T_i = K_i(T_b - T_i); \qquad \text{Equation 14a}$$

or $$K_i = \frac{\Delta T_i}{(T_b - T_i)}; \qquad \text{Equation 14b}$$

where $K_i$ depends on the geometry, the material properties of the catheter, the flow rate of the injectate injection and the blood flow velocity in the vessel; $T_b$ is the temperature of the blood flow, $T_i$ is the temperature of the injectate; and $\Delta T_i$ is the change in the dilution sensor temperature resulting from inside cooling by the injectate.

Figure 7:
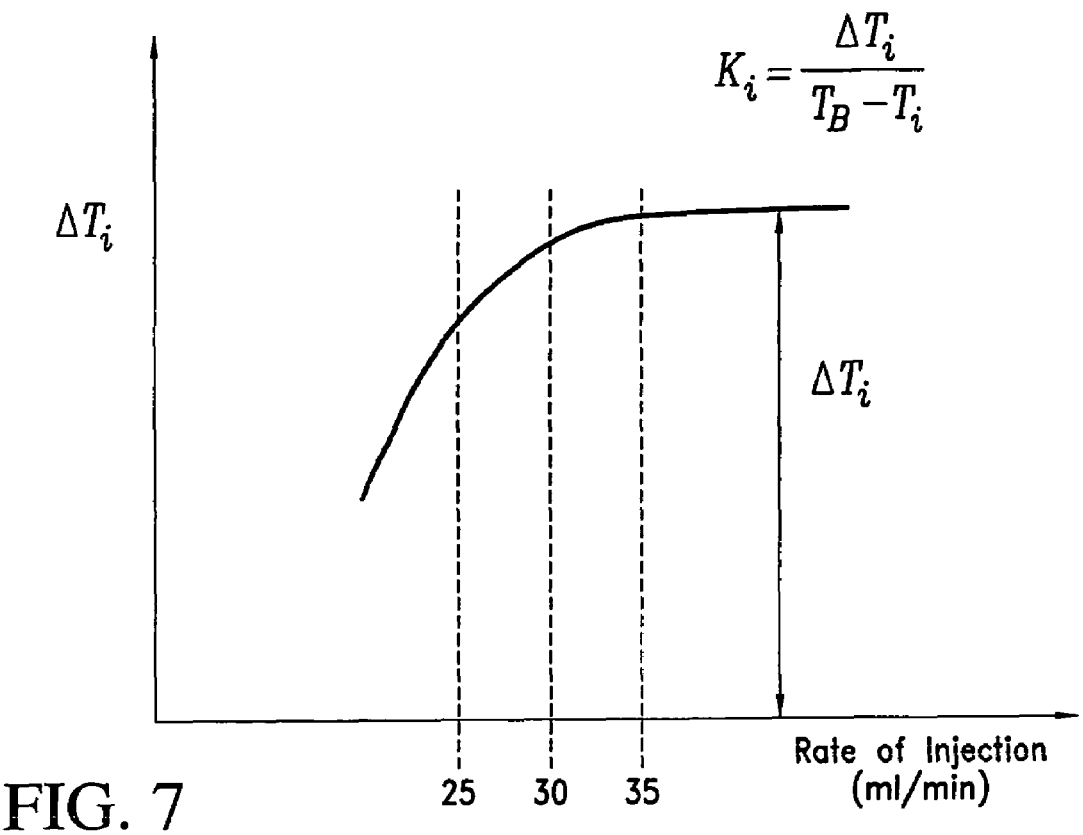
FIG. 7 is a graphical representation of the relationship between inside cooling ($K_i$, $\Delta T_i$) and the speed of the injection.

At a constant temperature difference ($T_b-T_i$) the value of $K_i$ is found to be dependent on the speed of the indicator injection (FIG. 7). For a particular 6 French catheter, it has been found that $K_i$ becomes practically independent from speed of injection (part 11 in FIG. 7), when the flow rate of indicator injection exceeded 30-40 ml/min. It is understood that in other catheter constructions, the value of flow at which $K_i$ becomes independent of the rate of injection can be different.

The pre calibration of a particular catheter or catheter style to minimize the effect of injectate induced temperature offset of a temperature dilution sensor can be accomplished by different coefficients and different procedures, wherein different equations can be derived, including equations corresponding to the equations set forth.

Figure 8:
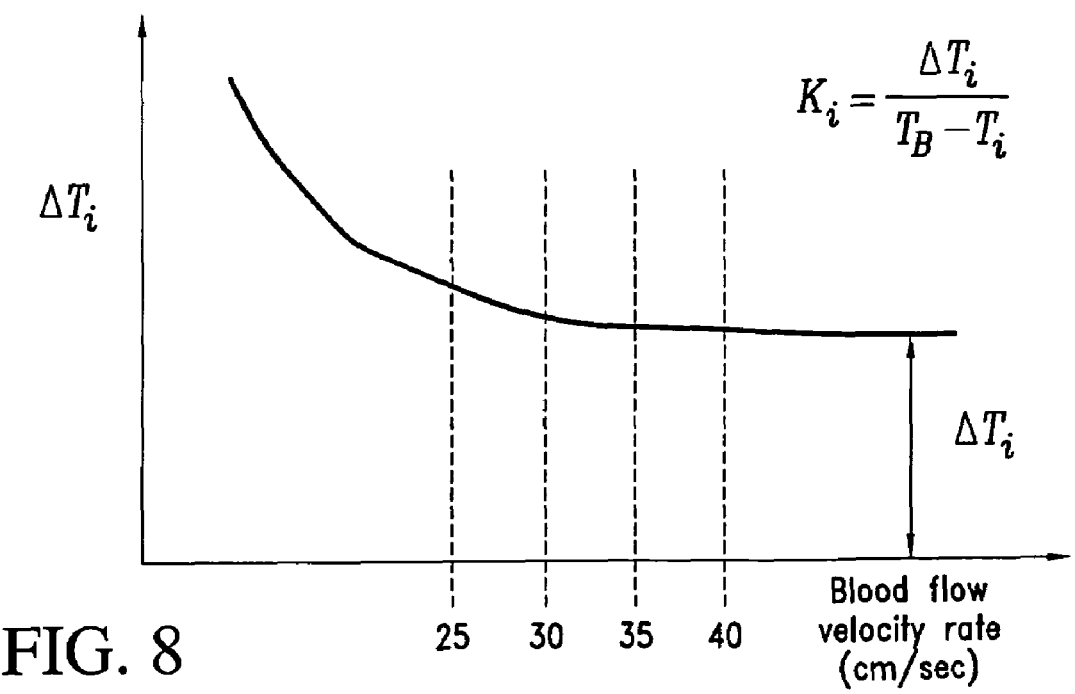
FIG. 8 is a graphical representation of the relationship between inside cooling ($K_i$, $\Delta T_i$) and blood velocity.

For example, the relationship of FIGS. 7 and 8 are illustrative and different relationships are possible. Thus, the calibration coefficient can be selected based upon estimated blood flow (velocity), and hence for a high blood flow, a smaller $K_i$ can be selected, and for a lower blood flow, a larger $K_i$ can be selected. Similarly, an injection rate that is measured (or determined from an injection curve or a dilution curve) can be the basis of a corresponding coefficient. It is understood the calibration coefficient can be adjusted in response to the blood flow rate or the injection rate of the injectate. That is, an initial calibration coefficient can be determined or estimated, wherein the initial calibration coefficient is modified in response to feedback from the actual flow or injection conditions. For example, if the blood flow rate is less than anticipated, the calibration coefficient can be increased. Conversely, if the blood flow rate is greater than anticipated, the calibration coefficient can be correspondingly decreased. These adjustments of the calibration coefficient in response to feedback from the actual system allows further increase in the accuracy of the measurements.

At a constant temperature difference ($T_b-T_i$) the value of $K_i$ is found to be dependent on the blood flow velocity (FIG. 8). For the particular 6 French catheter type, the value of $K_i$ becomes practically independent from blood velocity (part II of the curve) at 25-30 m/sec.

It is understood that in different catheter constructions, the value of the blood flow velocity when measurements become independent of injection speed may be different.

Figure 9A:
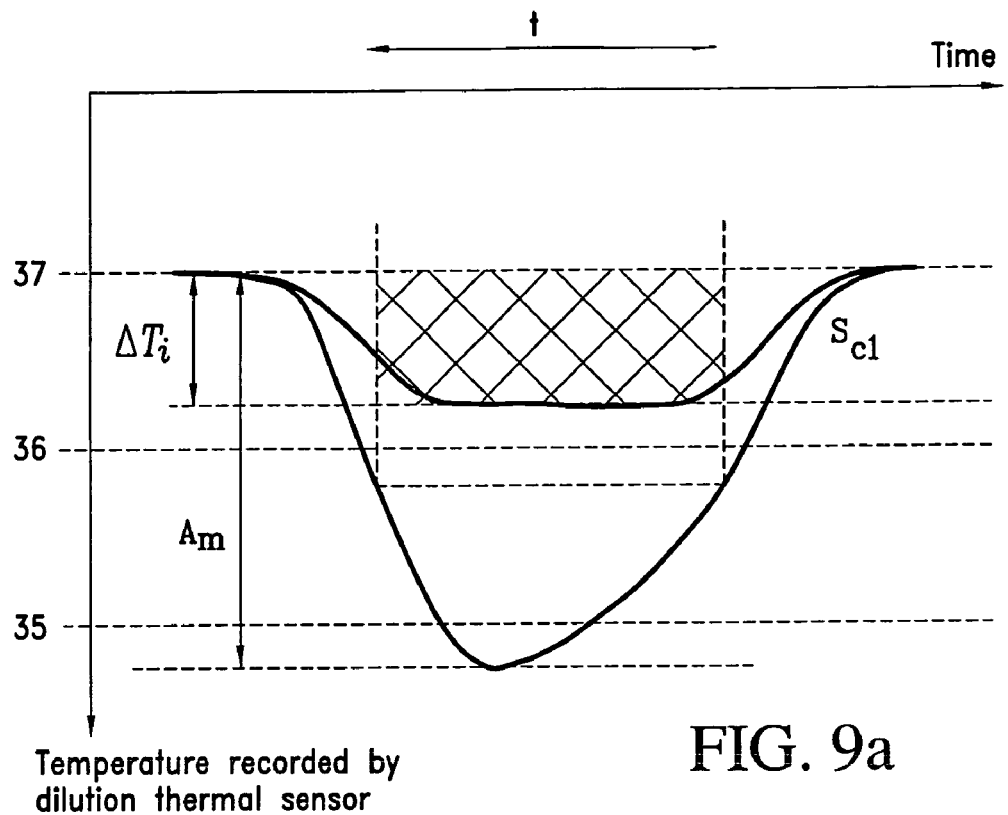
FIG. 9a is a graphical representation of a dilution curve, wherein area $S_c$ is approximated as a rectangle $S_{c1}$.
Figure 9B:
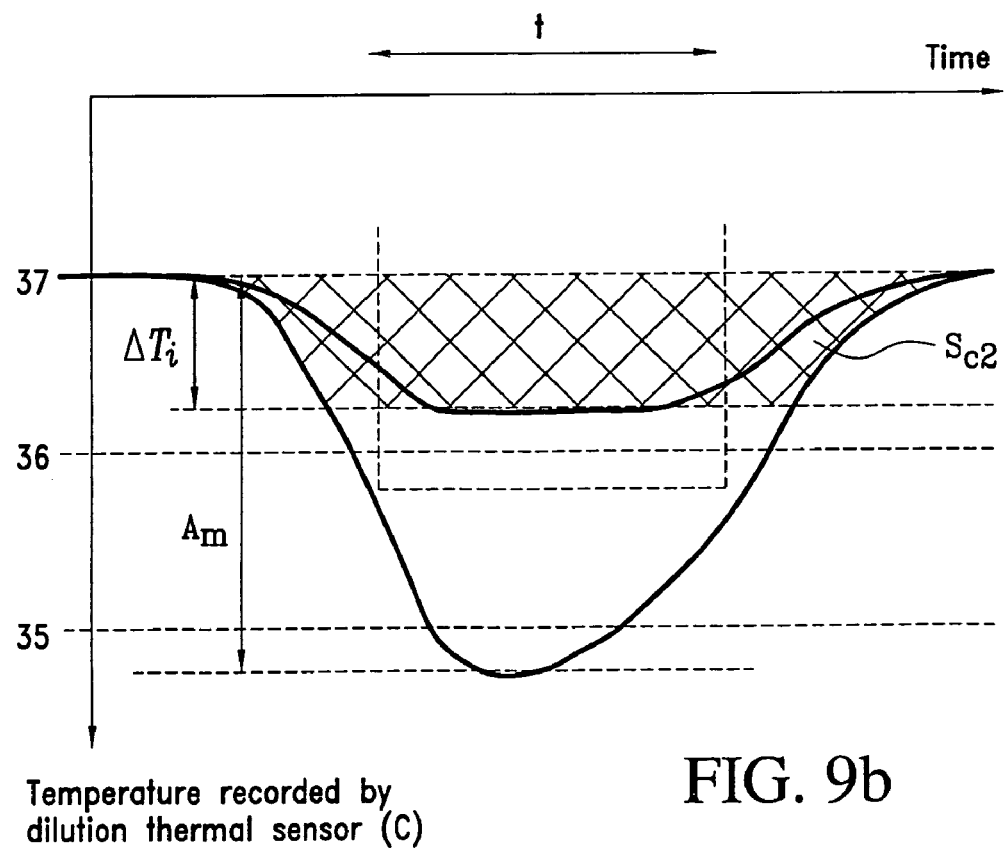
FIG. 9b is a graphical representation of a dilution curve, where area $S_c$ is approximated by $\Delta T_i$ and the shape of dilution curve ($S_{c2}$).

The shape of the curve that forms the area under the dilution curve $S_c$ (FIG. 6) is unknown for bolus injections. It can be expressed by different approximations (FIG. 9a, FIG. 9b, FIG. 9c) based on measured dilution curve parameters and a pre-calibrated value of $\Delta T_i$. For effectively continuous injections, the resulting dilution curve is shown in FIG. 9d.

Figure 3:
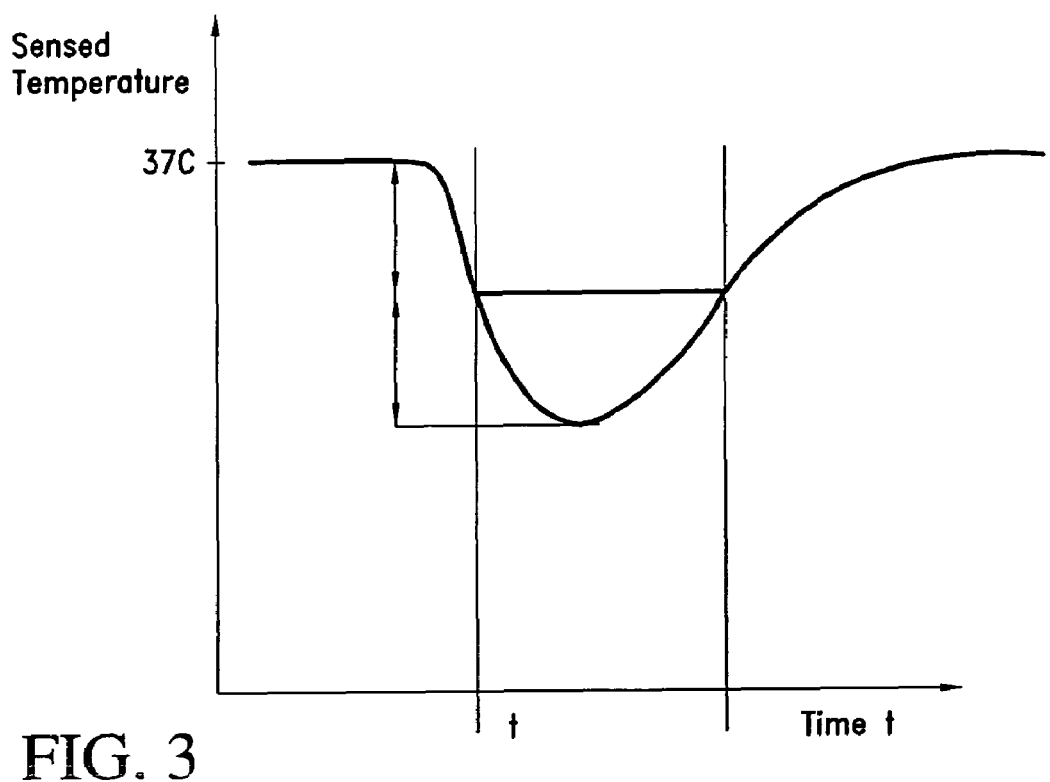
FIG. 3 is a graphical representation of the relationship between time and blood temperature by the dilution thermal sensor and measurement of injection time.

For a rectangular approximation (FIG. 9a), the value for $S_c$ can be expressed:

$$S_{c1} = \Delta T_i \times t \qquad \text{Equation 15a}$$

where t—is the duration of the injection (for example, the time width of the curve at the half height (FIG. 3).

From Equation 14a and Equation 15a:

$$S_{c1} = K_i \times (T_b - T_i) \times t \qquad \text{Equation 15b}$$

The value $K_i$ can be precalibrated for any particular catheter for different injection flow rates and for different, blood flow velocities in the blood flow to be measured. As it is clear from FIG. 7 and FIG. 8, the proper value of $K_i$ can then be substituted in Equation 15b during actual blood flow measurements based on the actual observed different flow conditions.

The second possible approximation of $S_c$ is the area $S_{c2}$ (FIG. 9b), that is limited by $\Delta T_i$ and actual shape of dilution curve.

Figure 9C:
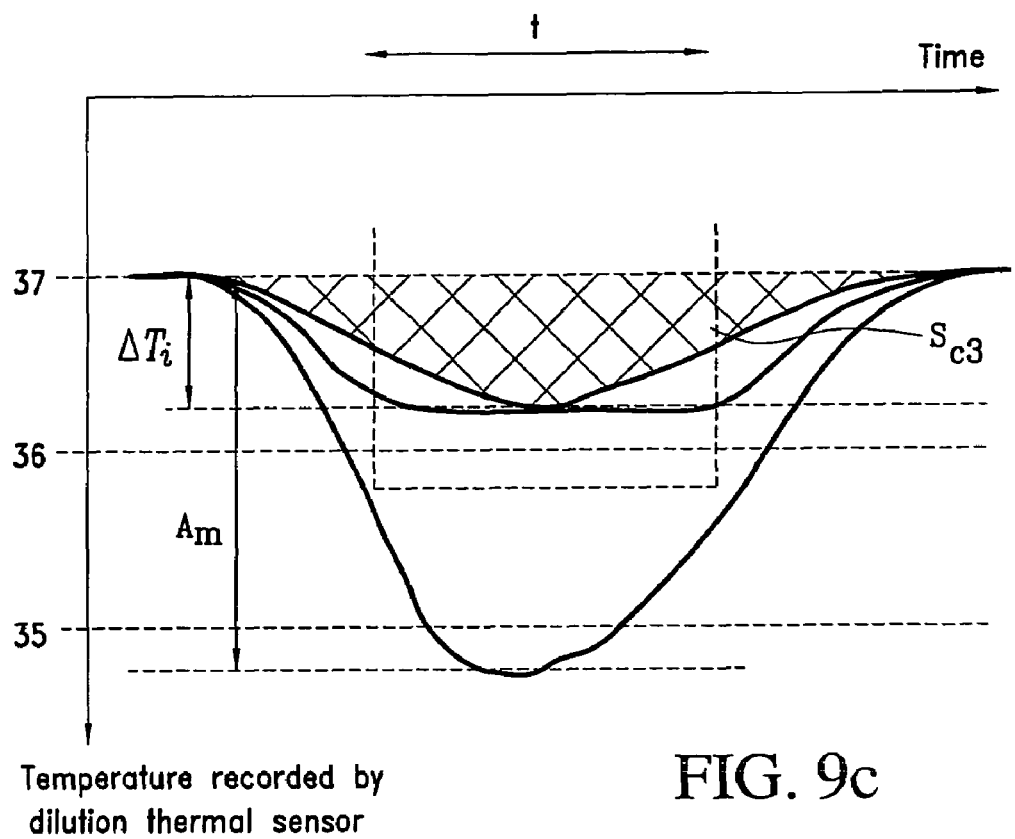
FIG. 9c is a graphical representation of a dilution curve, where area $S_c$ is approximated by the area $S_{c3}$ under the curve that has the same shape (similar) as the dilution curve but is proportionally smaller having maximum at $\Delta T_i$.
Figure 9D:
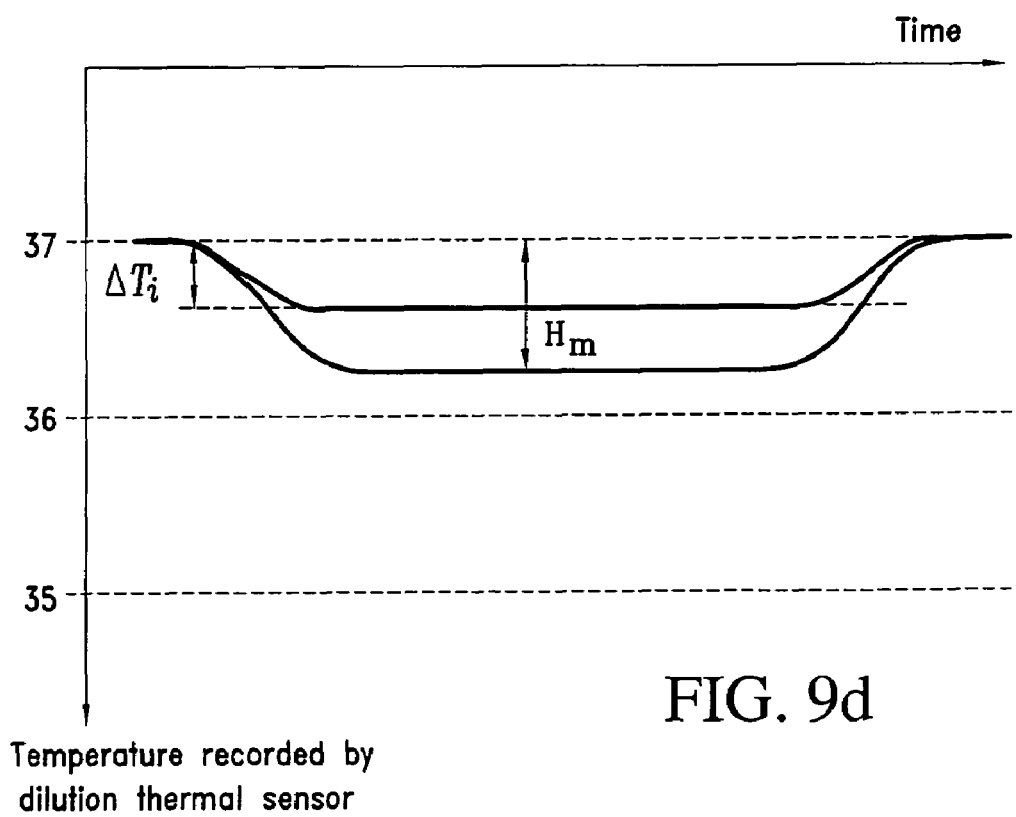
FIG. 9d is a graphical representation of a dilution curve, with a continuous infusion, where the measured temperature shift is $H_m$.

The third possible approximation of $S_c$ is the area $S_{c3}$ (FIG. 9c) that has a similar shape as the actual dilution curve but is proportionally smaller with its maximum at $\Delta T_i$:

$$S_{c3} = S_m \left( \frac{\Delta T_i}{A_m} \right) \qquad \text{Equation 16}$$

where $A_m$ is the maximum of actual measured dilution curve (FIG. 9c).

In a further refinement, one could mathematically combine the calculated values of $S_{c1}$, $S_{c2}$ and $S_{c3}$ to produce an actual value of $S_c$ that provides an optimal blood flow measurement accuracy. For example, the actual value of $S_c$ can be considered as an average of $S_{c3}$ and $S_{c2}$:

$$S_c = \frac{(S_{c2} + S_{c3})}{2}$$

It is understood different approximations and different combinations of the approximation presented above and others can be used to estimate $S_c$ for use in Equation 13.

Referring to FIG. 9d it is also recognized the introduction of the injectate can effectively be continuous, whereupon the difference in areas under the curves can be obtained by subtracting the measured temperature.

In the case of continuous infusion of the indicator, Equation 13 may be rewritten as:

$$Q_f = \frac{kq(T_b - T_i)}{(H_m - \Delta T_i)} - Q_i^* \qquad \text{(Equation 13a)}$$

where q—rate of indicator infusion in ml/min; $H_m$—is the total change in the temperature; $\Delta T_i$—is the portion of the change related to the inside cooling effect (FIG. 9d), $Q_i^*$ adjustments for injection flow $Q_i$.

The above and other theoretical and experimental observations show that the following primary ways can be used to improve blood flow measurement accuracy of the retrograde catheter in the presence of the inside cooling effect:

1. Pre-calibration of the thermal conductive properties of the catheter to determine $K_i$ over the range of user conditions, and use of this data to adjust recorded signals from the thermal sensors;

2. A plurality of injections of different volumes or different time length from which the inside cooling effect on the dilution thermal sensor and/or the injectate temperature can be calculated;

3. A plurality of thermal sensors, where the magnitude of the inside cooling effect on the dilution thermal sensor is measured by an additional thermal sensor and compensated;

4. A plurality of pre calibrated thermal sensors, are used to simultaneously eliminate the necessity of measuring the injectate temperature and the effect of inside cooling.

5. Creating special construction of the catheter that will enhance or maximize the thermal isolation of the injectate lumen from the dilution thermal sensor;

6. Any combination of the above.

1. Pre-calibration of the Thermal Conductive Properties of the Catheter to Determine $K_i$ Over the Range of User Conditions and Use of this Data to Adjust Recorded Signals from the Dilution Sensor.

As seen from FIG. 7 and FIG. 8, the temperature changes due to inside cooling for a particular catheter construction can be determined by bench studies. From these value of $K_i$ as a function of injectate flow rate and the blood flow velocity can be determined. The experimentally determined values of $K_i$ are used with Equation 13 to estimate $S_c$ and thus compensate for the inside cooling effect, or error. The values related to FIG. 7 and FIG. 8 can be simply determined by placing the catheter in a bench model of the A-V shunt not facing the blood flow but with the flow. In this case, the injected indicator (injectate) (such as saline) will cool the dilution sensor 36 from the inside prior to exiting through the ports and will then be flushed away from the catheter, so the signal recorded by the dilution sensor 36 will be related only to the inside cooling effect which produces the area curve with area $S_c$. The relationship of FIG. 7 and FIG. 8 will be obtained by changing the speed of injections and flow rate in the A-V shunt model.

The equation for measuring blood flow using such a pre-calibrated sensor for example for rectangular approximation (FIG. 9a and Equation 15b) will be from Equation 13:

$$Q_f = \frac{kV(T_b - T_i)}{(S_m - K_i \times (T_b - T_i) \times t)} \qquad \text{Equation 17}$$

In this expression k, and $K_i$ are known from pre-calibration; $T_b$, $T_i$, $S_m$ and t are measured from the dilution curve and injectate sensor, and V is the predetermined volume of injection. The value of $Q_f$ can thus be determined.

2. A Plurality of Injections of Different Volumes or Different Time Length from which the Inside Cooling Effect on the Thermal Dilution Sensor and/or Injectate Temperature can be Calculated.

The area under the measured indicator dilution curve $S_m$ is again considered to consists of two parts ($S_m = S_{dil} + S_c$) (see FIG. 6). The first part ($S_{dil}$) is produced by the actual blood dilution and for the same blood flow is proportional to the volume of the injection. The second part, $S_c$, is proportional to $\Delta T_i$ and the length of injection, but not to the volume of the injection (injectate) (see FIG. 7).

For two injections of different volumes, $V_1$ and $V_2$, made at different times, Equation 17 yields, for example for rectangular approximation, Equation 15b):

$$Q_f = \frac{kV_1(T_b - T_i)}{(S_{m1} - K_i \times (T_b - T_i) \times t1)} \quad \text{Equation 18a}$$

$$Q_f = \frac{kV_2(T_b - T_i)}{(S_{m2} - K_i \times (T_b - T_i) \times t2)} \quad \text{Equation 18b}$$

where $S_{m1}$ and $S_{m2}$ are the measured areas under the dilution curves from the first and second injections, respectively, and t1 and t2 are the length of the first and the second injections, respectively.

In Equations 18a and 18b the values: $S_{m1}$, $S_{m2}$, t1, t2, and $T_b$ are measured from the dilution curves, and the values: $V_1$, $V_2$, k, and $T_i$ are known. Thus, having two equations with two unknowns, $Q_f$ and $K_i$, provides that the equations can be solved to measure blood flow $Q_f$ with no pre-calibration procedure.

Alternatively, if $K_i$ is known from pre-calibrations, but the temperature of injection $T_i$ is unknown (i.e., using a configuration without injectate temperature sensor), then again $Q_f$ can be calculated from these same equations.

3. A Plurality of Thermal Dilution Sensors where the Magnitude of the Dilution Sensor Inside Cooling Effect is Measured by an Additional Thermal Sensor and Compensated.

The basis of this approach is that the catheter 10 can be designed to have two or more thermal dilution sensors 36 that are in different conditions regarding the inside cooling effect and the outside diluted blood cooling. Readings from these thermal sensors can be compared to compensate or minimize the inside cooling effect on the accuracy of blood flow measurement. For example, the catheter 10 can be designed such that one sensor is influenced by both inside cooling and blood dilution cooling. The second thermal sensor is influenced dominantly only by inside cooling (FIG. 10) with no dead space or with dead space (FIG. 11).

Figure 10:
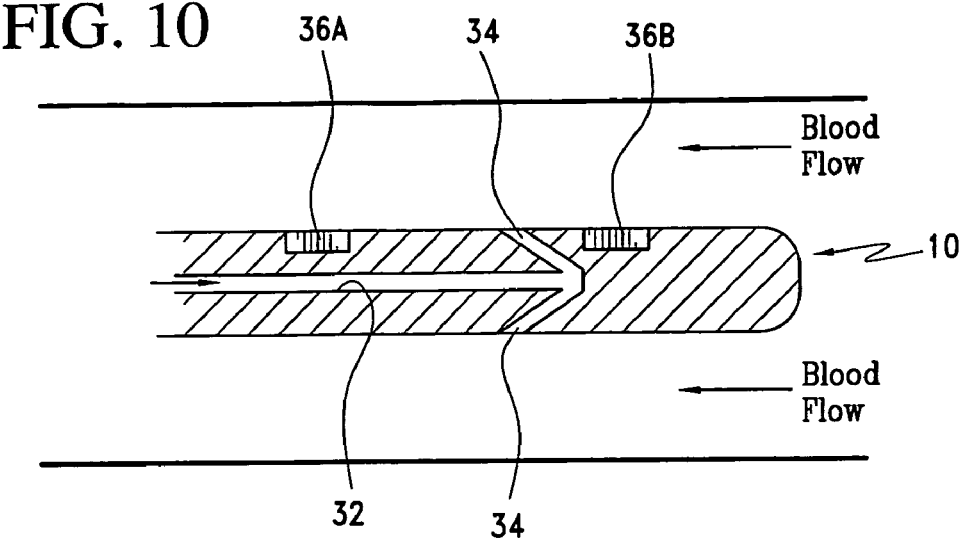
FIG. 10 is a cross sectional view of a thermodilution catheter having a two sensor compensation system with a distal thermal sensor subject to reduced temperature influence of outside dilution [without dead space].
Figure 11:
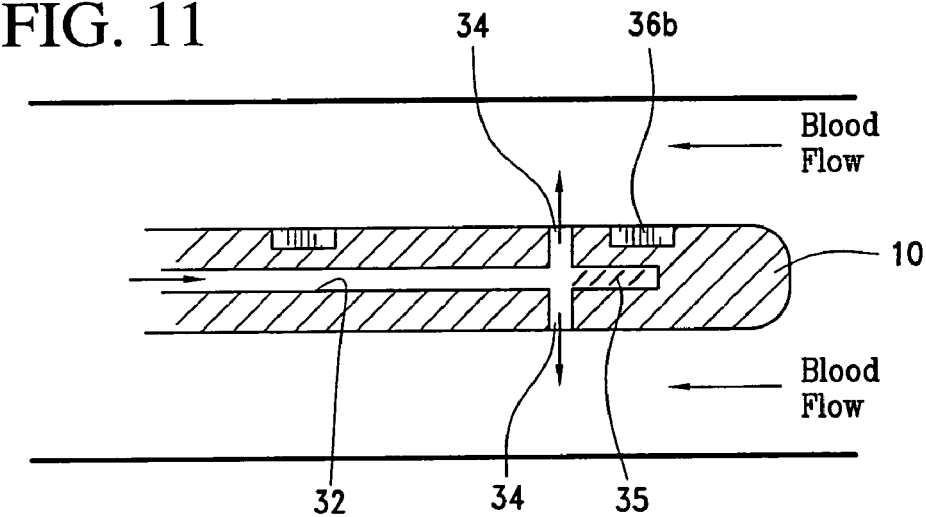
FIG. 11 is a cross sectional view of a thermodilution catheter having a two sensor compensation system with a distal sensor no influence of outside dilution (with dead space).

In FIG. 10, the indicator (injectate) passes both thermal sensors from the inside of the catheter, but the angled apertures dictating the place where the indicator enters the blood stream downstream of the distal thermal sensor 36b (i.e., the sensor close to the catheter tip) and thus, the signal from the distal thermal sensor is influenced only by inside cooling. If the catheter 10 is designed such that the thermal conductance from the injectate channel is the same for both sensors, then blood flow can be calculated through the difference of the temperature changes recorded by the two sensors analogous to Equation 17. Specifically:

$$Q_f = \frac{kV(T_b - T_i)}{(S_{mp} - S_d)} \quad \text{Equation 19}$$

where $S_{mp}$ and $S_d$ are the areas under dilution curves from the proximal and distal sensor, respectively.

It may be useful to design the catheter 10 such that the indicator injection will introduce turbulence into the channel within catheter and/or the measured blood flow. This turbulence will create circulation in the dead zone (FIG. 11) so that indicator (injectate) will flow along the sensing zone of the distal thermal sensor 36b. This turbulence can be achieved by changing the angle of apertures of the catheter injection holes with respect to the main channel, or by introducing discontinuities within the injectate lumen for example by creating spiral ribs 35 within.

Figure 12:
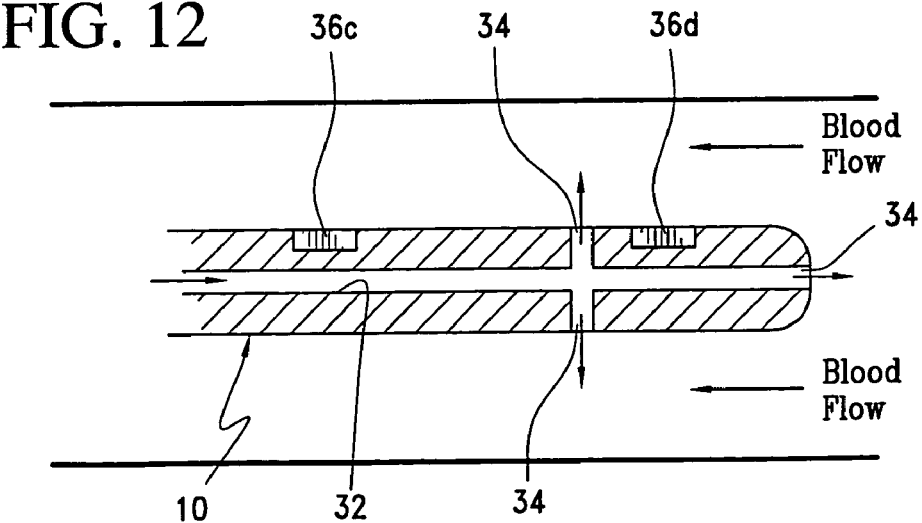
FIG. 12 is a cross sectional view of a thermodilution catheter with a two sensor compensation system with different influence of outside and inside cooling on the thermal sensors.

An alternative way of compensation is presented in FIG. 12. Here, the catheter 10 is equipped with two thermal dilution sensors 36c, 36d, positioned as shown. The total injected volume of indicator (injectate) V is distributed between the distal injection port with aperture (a×V) and the proximal port(s) with total aperture V(1−a), where "a" is the percentage or portion of the indicator that leaves the catheter through the distal injection port.

The distal thermal dilution sensor 36d will be cooled by two sources, firstly from the inside, while the volume (a×V) passes; and secondly by the blood cooled by volume a×V from the outside of the catheter after mixing with blood:

$$Q_f = \frac{kV \times a(T_b - T_i)}{(S_{md} - K_{id} \times (T_b - T_i) \times t_d)} \quad \text{Equation 20}$$

where $S_{md}$ is the total area under dilution curve of the distal thermal sensor. The second part of the sum in denominator is related to the area under dilution curve on the distal thermal dilution sensor due to the indicator passing through the lumen inside the catheter; where index "d" means distal sensor.

The proximal dilution sensor 36c will be also cooled by two sources, firstly from the inside while the volume (V) passes; and secondly by the blood cooled by volume V from the outside of the catheter after mixing with blood:

Both these effects are caused by same total injected volume V.

$$Q_f = \frac{kV(T_b - T_i)}{(S_{mp} - K_{ip} \times (T_b - T_i) \times t_p)} \quad \text{Equation 21}$$

where $S_{mp}$ is the total area under dilution curve of the proximal sensor. The second part of the sum in denominator is related to the area under dilution curve on the proximal thermal dilution sensor due to the indicator passing through the lumen inside the catheter; where index "p" means proximal thermal sensor.

Subtracting the temperature readings of these two thermal sensors and considering that the inside cooling effect is the same on both sensors, Equations 20 and 21 yield:

$$Q_f = \frac{kV(1-a)(T_b - T_i)}{(S_{mp} - S_{md})} \quad \text{Equation 22}$$

This approach offers the advantage that $K_i$ is eliminated from the flow equation; therefore no pre-calibration value $K_i$ for both thermal sensors is determined. In practice, if the inside cooling effect is not the same for these two sensors (making $K_{ip}$ not equal to $K_{id}$) this difference should be considered while combining Equation 21 from Equation 20.

4. A Plurality of Pre-calibrated Thermal Sensors, to Simultaneously Eliminate the Necessity of Measuring the Injectate Temperature and the Inside Cooling Effect.

The basis of this approach is that two thermal dilution sensors are employed in a catheter construction, where the sensors exhibit different sensitivity to the inside cooling effect from the injectate and the outside blood dilution cooling. Comparing the data from these thermal sensors helps to eliminate the influence of the injection (injectate) temperature and effect of inside cooling.

Equation 17, and Equation 14 can be written for two thermal sensors "1" and "2":

$$Q_f = \frac{kV(T_b - T_i)}{(S_{m1} - K_{i1} \times (T_b - T_i) \times t)} \quad \text{Equation 23a}$$

$$Q_f = \frac{kV(T_b - T_i)}{(S_{m2} - K_{i2} \times (T_b - T_i) \times t)} \quad \text{Equation 24b}$$

where $S_{m1}$ and $S_{m2}$ are known areas under dilution curves from the first and second sensor; $K_{i1}$ and $K_{i2}$ are pre-calibrated coefficients for first and second thermal sensor respectively (see Equation 21), (FIG. 7); Solving these equations for $Q_f$ yields:

$$Q_f = \frac{kV(S_{m1} - S_{m2})}{(S_{m2} \times K_{i1} - S_{m1} \times K_{i2})} \quad \text{Equation 25}$$

As is seen from the above equation, this approach eliminates the necessity of a separate thermal sensor for injectate temperature measurement.

5. Creating a Special Construction of the Catheter that Will Enhance and/or Maximize the Thermal Isolation of the Injection Lumen from the Thermal Dilution Sensor.

Figure 13A:
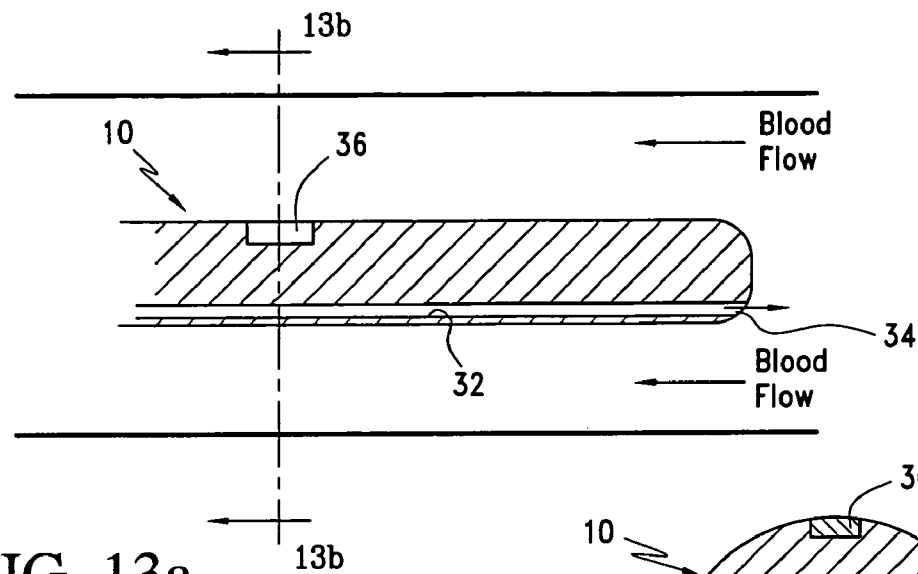
FIG. 13a is a cross sectional view of a thermodilution catheter with the thermal sensor spaced from an injectate channel and injection port.
Figure 13B:
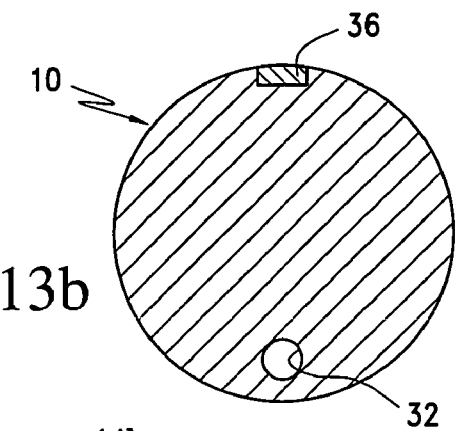
Figure 14A:
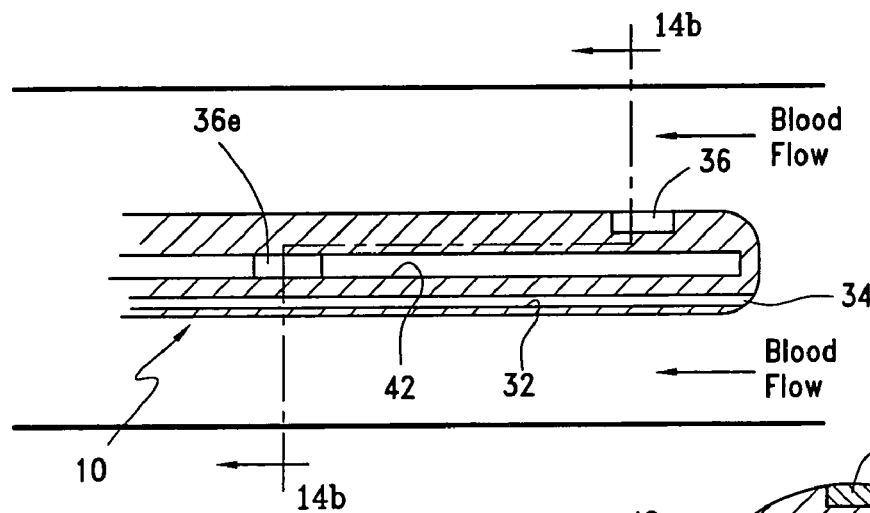
FIG. 14a is a cross sectional view of a thermodilution catheter with the inclusion of the air gap between the dilution thermal sensor and the injectate channel, and the injectate thermal sensor located inside the air gap channel.
Figure 14B:
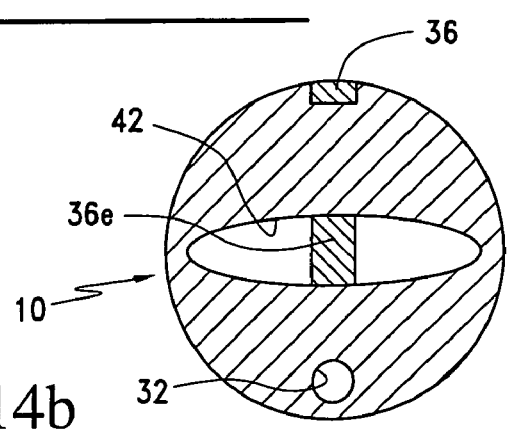

Another way to minimize the influence of the temperature of injected indicator (injectate) is to thermally separate the injection (injectate) lumen as far as possible from the thermal dilution sensor 36 as seen in FIG. 13. That is, the catheter 10 is constructed to enhance thermal isolation of the thermal sensor from the injectate flowing within the catheter. Specifically, the conductive heat path can be minimized by locating a spacer lumen, or gap 42 of relatively high resistance to heat conduction between the injectate lumen and the thermal sensor 36. The construction of the catheter 10 can include a thermal insulating gap as seen in FIGS. 14a and 14b that is filled with air, gas or another low heat conducting material, foam, material having a greater insulation value than the material defining the catheter. It is also contemplated the insulating gap can include a void holding vacuum. It has been found that a significant reduction of the inside-cooling coefficient is observed for two different catheter geometries. The introduction of an air gap between the distal thermal sensor and indicator (injectate) lumen decreased the $K_i$ from $K_i \approx 40\%$ at the high blood velocity rates to $K_i \approx 4.3\%$. As set forth, by employing the insulating gap (or lumen), the inside cooling effect from the injectate can still be measured and further eliminated by a separate thermal sensor by pre-calibration of the sensor.

Figure 15A:
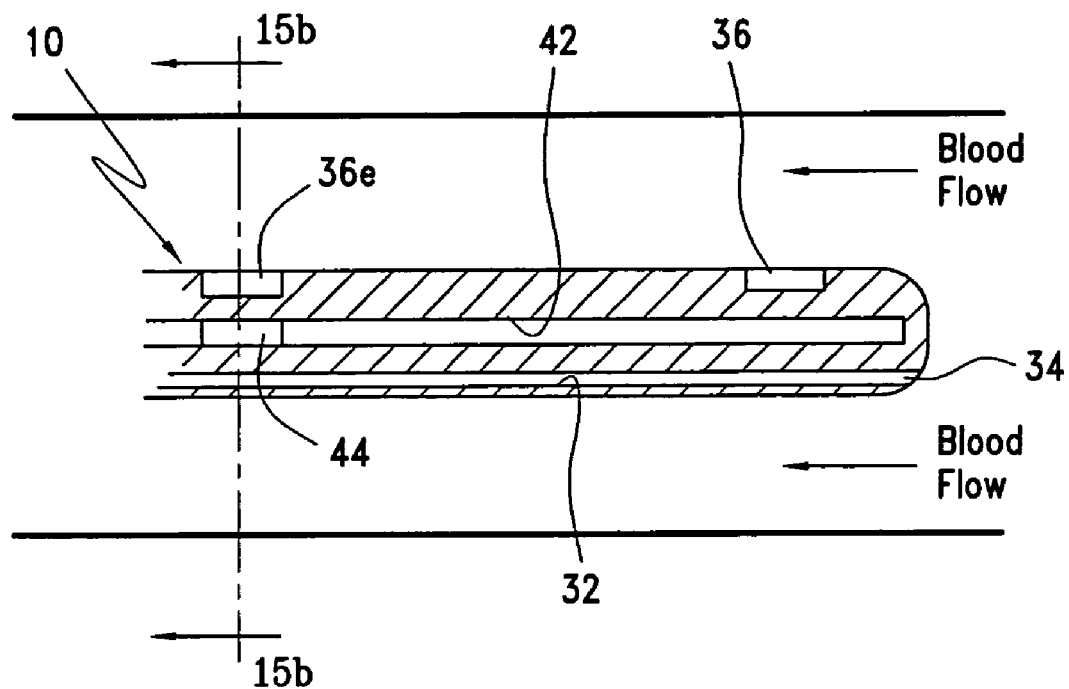
FIG. 15a is a cross sectional view of a thermodilution catheter where both thermal sensors are located in one lumen, with an air gap between the dilution thermal sensor and the injectate lumen and a closed air gap (thermal conductor) between the injectate thermal sensor and the injectate lumen.
Figure 15B:
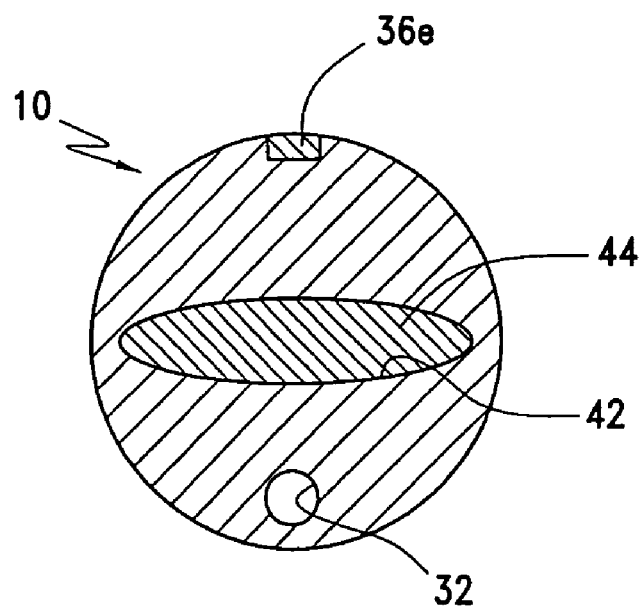

A thermal insulating gap such as an inside air lumen can be used to place the injection (injectate) temperature sensor (FIG. 14) to be thermally proximal to injection (injectate) lumen. In FIG. 14, the injectate temperature thermal sensor 36e can accurately measure the temperature of the injectate. The dilution sensor 36 is located downstream of the introduction port to sense the diluted blood flow. Alternatively, (as seen in FIG. 15) the injection temperature thermal sensor 36e can be located in the same lumen as the distal thermal sensor but the air gap (insulating spacer) can be eliminated, or for example filled with a thermal conductor such as a plastic, or the material of the catheter, to improve heat conductance (FIG. 15) at the location of the injection temperature thermal sensor 36e. The thermal conductor has a greater thermal conductivity than the insulating lumen, and preferably has a thermal conductivity at least as great as the material of the catheter.

The thermal isolation is directed to thermally separating the thermal dilution sensor from the indicator (injectate) temperature. Therefore, the present construction is in contrast to the prior constructions of a coaxial catheter which is not retrograde, as the inside catheter was used to inject indicator that will have maximum isolation from the outside blood so as not to be heated prior entering blood. That is, in the prior construction of a coaxial catheter, wherein the entire indicator lumen is thermally spaced from the surrounding blood flow, the present catheter thermally isolates the thermal dilution sensor 36 from injectate flow through the injectate (indicator) lumen, maximizing the thermal resistance between the injectate in the catheter and the thermal sensor. Specifically, in prior coaxial constructions having a radial dimension of the annulus between the injectate and the thermal sensor, the present construction allows effectively twice the radial dimension of the coaxial construction to be disposed intermediate the injectate in the catheter and the temperature sensor. That is, the entire cross sectional area of the thermally insulating spacer, gap, is located intermediate the injectate lumen and the temperature (thermal dilution) sensor. The present construction allows a reduced catheter cross sectional area with enhanced thermal insulation between the thermal dilution sensor and the injectate lumen, and thus allows the catheter to be employed with less adverse effect on the measured flow.

For example, the catheter 10 can have an insulating lumen intermediate the dilution sensor and the injectate lumen. In this construction it is also possible to locate the injectate temperature sensor within the insulating lumen, thereby exposing the injectate temperature sensor to the thermal effect of the injectate passing within the catheter, and the dilution sensor is located to dispose the insulating lumen intermediate the injectate lumen and the dilution sensor. This creates differing thermal conductive properties between the dilution sensor and the injectate sensor.

Alternatively, the injectate temperature sensor can be located at a position spaced from the insulating lumen, wherein a portion of the insulating lumen includes a thermal conductor to thermally link the injectate temperature sensor and the injectate lumen.

In a catheter having a generally circular cross section, the thermal dilution sensor is spaced from the injectate lumen by a radius of the cross section. In one configuration, the cross sectional area of the catheter intermediate the thermal dilution sensor and the injectate lumen is maximized. It is also understood, at least 50% of a cross sectional dimension of the catheter can be located intermediate the injectate lumen and the thermal sensor, with a preferred construction providing at least 70% of catheter cross section dimension being located intermediate the thermal dilution sensor and the injectate lumen. However, as much as 90 to 95% of the cross sectional dimension could be located intermediate the thermal dilution sensor and the injectate lumen.

An alternative construction locates the insulating lumen intermediate the thermal dilution sensor and the injectate lumen so that along a given chord of the catheter cross section, the insulating lumen defines a greater portion of the chord than the material of the catheter. In a preferred construction the insulating lumen defines at least 50% of the chord length, with a more preferred construction having the insulating lumen define at least 75% of the chord length, with a more preferred insulating lumen defining 80% of the chord length. By increasing the percentage of a chord length defined by the insulating lumen, the thermal isolation of the thermal dilution sensor can be increased. That is, the amount relatively thermally conductive material of the catheter available for heat transfer is minimized.

6. Any Combination of the Above.

The accuracy of blood flow measurements by a retrograde catheter by compensation of inside cooling (or heating) from injectate flow through the catheter can be improved by employing any of (i) the precalibration of the thermal conductive properties of the catheter; (ii) employing a plurality of different injections; (iii) employing a plurality of dilution sensors; (iv) employing pre-calibrated thermal sensors or (v) thermally isolating the dilution sensor from injectate flowing within the catheter.

(ii) Measuring the Temperature of Injected Indicator

In thermodilution measurements of cardiac output, a first distal thermal sensor is located in the pulmonary artery and produces dilution curves, and a second thermal sensor is located in the central vein, in the aperture (or within the aperture) through which indicator solution enters the blood stream. In this way, the second thermal sensor measures the temperature of the solution (injectate) entering the blood. In the present case, the existence of multiple small injection ports increases the technological difficulty locating a thermal sensor within the space of the introduction port. If the thermal sensor is not located immediately near or adjacent the introduction port, the temperature of the thermal sensor will be influenced by both the injected indicator (injectate) and the blood temperature, thereby decreasing the accuracy of the resulting measurement.

To solve this problem of measuring $T_i$, a second proximal thermal sensor 36a (FIG. 1, 2) for measuring the temperature of the indicator injection (injectate) is located in a part of the catheter 10 that is out of the blood stream. In this case, the temperature of injected indicator is measured just prior to the indicator entering the part of the catheter that is located in the blood stream. The heating/cooling of the indicator while passing through the length of the catheter that is in thermal contact with the blood flow of the A-V shunt (before exiting through ports into the blood flow) is negligible or can be accounted. Also, the surrounding air has a relatively low thermal conductance (in contrast to the flowing blood) and the thermal sensor 36a will more accurately represent temperature $T_i$. It is also noted that the volume of the indicator injection V must be sufficiently large to be significantly greater than a priming volume of any liquid contained in the portion of the injection lumen that is located within the blood vessel and thus has a temperature that is approximate to the temperature of the blood.

Figure 16:
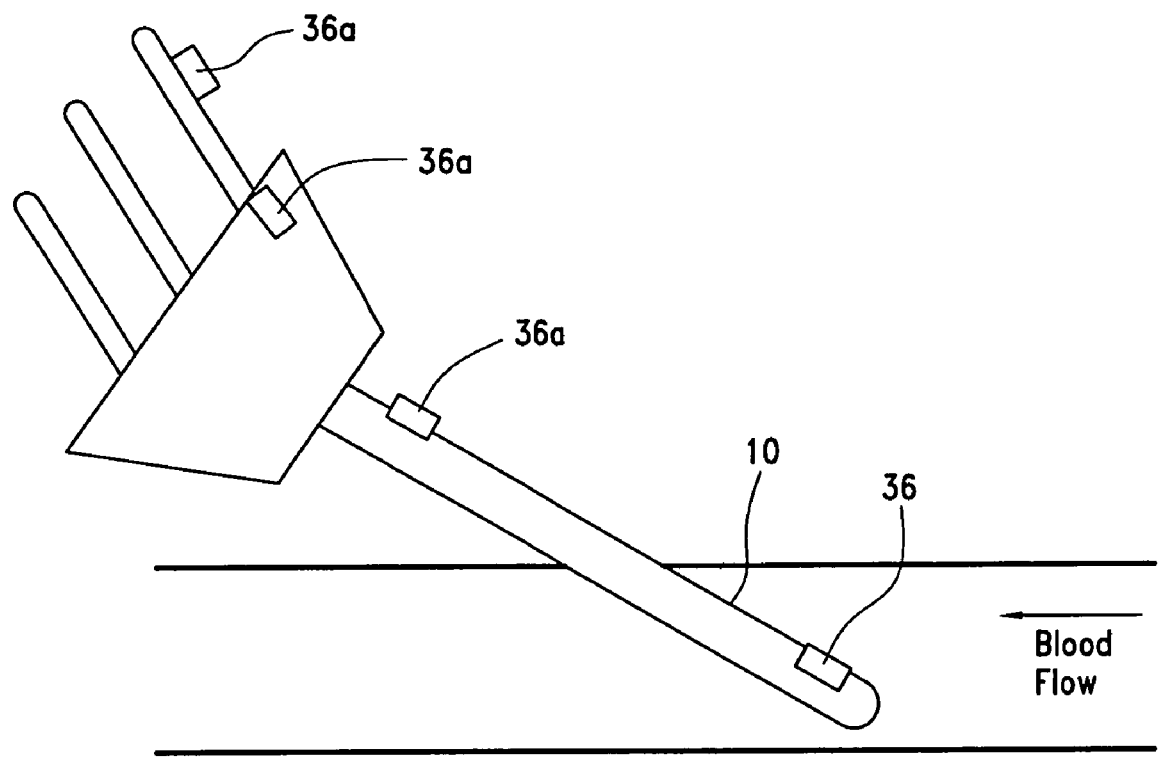
FIG. 16 is a cross sectional view of a thermodilution catheter with the injectate thermal sensor placed in at least one of the manifold, the injection side arm, the injection sides arm or the catheter so that the thermal sensor is separable from the catheter.

The thermal sensor 36a measuring the injection (injectate) temperature can be also located out of the body of the catheter 10, such as on the tubing leading to manifold or inside manifold (FIG. 16). Alternatively, the thermal sensor 36a for measuring the injected indicator can be attached to the tubing line or the catheter 10. The advantage of attaching the second thermal sensor 36a out of the body of the catheter is the elimination of the additional lumen for communicating with the sensor. That is, if the sensor 36a were located inside the catheter body, the existing lumens would be of a smaller cross sectional area to accommodate the need for the lumen corresponding to the sensor. This allows the catheter to have a smaller cross sectional area and thus can be used for smaller A-V shunts or smaller other vessels, which may be 6 French or less, with less influence on the initial blood flow due to it smaller size.

Attaching the thermal sensor 36a (FIG. 16) can reduce the cost of the catheter, as the attached sensor is not part of a single use catheter and thus can be reusable.

The plastic or catheter material between the injection lumen and the injection thermal sensor (thermistor) does not reach the temperature of the indicator, for some period of time. In some cases, while the operator is waiting for the injection of the indicator (injectate), blood migrates up through injection channel (lumen) and reaches the injection thermal sensor and heats the thermal sensor and the surrounding material of the catheter prior to injection. To minimize these errors, the minimal temperature is chosen to be $T_i$ during injection time (taken from the distal sensor in the blood).

In a further configuration, the catheter body includes a thermal dilution sensor lumen, which can receive electrical leads to the thermal dilution sensor as well as the thermal dilution sensor. The catheter body also includes the injectate lumen and the thermal insulating lumen. The catheter body can include the thermal insulator including a portion of the thermal insulating lumen, thereby effectively receiving a corresponding length of the insulating lumen. The thermal injectate sensor can be located adjacent the thermal conductor to thereby respond to the temperature of the injectate in the injectate lumen. The thermal injectate sensor can be located in the insulating lumen, the catheter body or the thermal dilution sensor lumen to be adjacent the thermal insulator (in the thermal insulating lumen), and thereby provide a signal corresponding to the temperature of the injectate in the injectate lumen.

1. Thermodilution Catheter Placed with the Blood Flow

Figure 17:
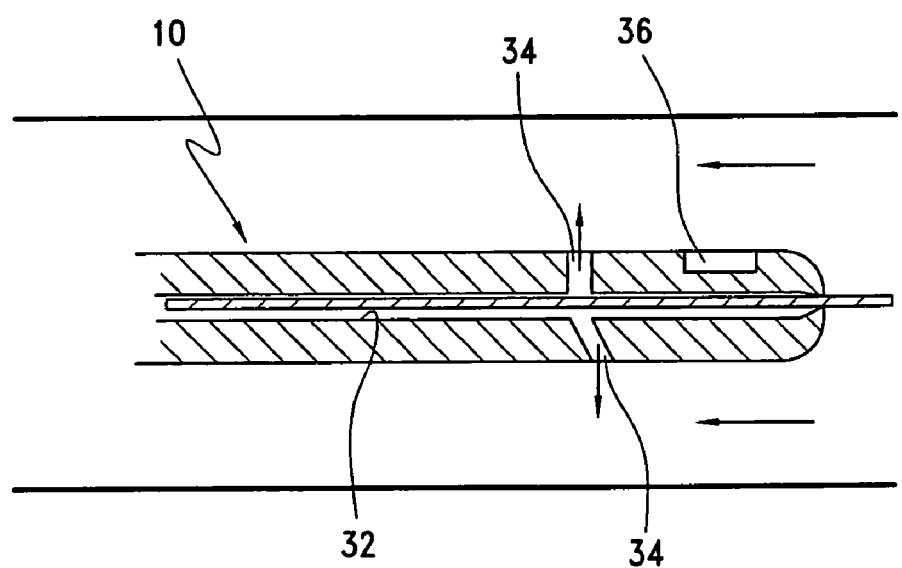
FIG. 17 is a cross sectional view of a thermodilution catheter with the narrowing at the tip of the injectate lumen, such as a guide wire port in a guide wire lumen.

Measuring blood flow in the peripheral arteries, such as the kidney artery requires minimization of the catheter size to eliminate the influence on initial blood flow. The relatively large size of a catheter, especially located in the narrowing site of the blood vessel may decrease the blood flow and introduce inaccuracies into measurements. In this situation, it is beneficial to minimize the constructive elements of the catheter. For example, it is advantageous to use the lumen that is used for the guide wire as a lumen for injection of the indicator, as seen in FIG. 17. In this situation, part of the introduced injectate volume will exit the catheter 10 downstream of the thermal sensor and the actual value of V in Equation 1 will be different. To minimize this effect, the lumen at the distal tip of the catheter can be made narrower than the remaining part of the lumen. The distribution of the injected volume V in the particular catheter constriction can be estimated with prior bench tests.

$$Q = \frac{k(T_b - T_i) \cdot V(1-a)}{S} \qquad \text{Equation 25}$$

where "a" is the portion of indicator that passes from the catheter through the distal aperture in the guide wire lumen.

Measurements while the guide wire is inside the catheter 10 will substantially reduce the error because the distal aperture will be substantially blocked by the guide wire. The value of "a" for this situation must be separately evaluated in the bench studies. An additional source of error may appear due to the fact that while the indicator is passing the thermal sensor, the indicator may cool the thermal sensor from inside, thereby introducing error in the measurements:

$$Q = \frac{k(T_b - T_i) \cdot V(1-a)}{(S_m - S_{in})} \quad \text{Equation 26}$$

where $S_m$—is the total area under the dilution curve; and $S_{in}$—the part of the area under dilution curve related to the cooling of the distal sensor from the inside of the catheter.

While a preferred embodiment of the invention has been shown and described with particularity, it will be appreciated that various changes in design and formulas and modifications may suggest themselves to one having ordinary skill in the art upon being apprised of the present invention. It is intended to encompass all such changes and modifications as fall within the scope and spirit of the appended claims.

The invention claimed is:

1. A method of enhancing determination of a blood flow rate in a conduit, the method comprising compensating for an injectate induced thermal offset of a first thermal dilution sensor connected to a retrograde catheter, the injectate induced thermal offset resulting from travel of the injectate through the catheter, the compensating including at least one of employing (i) a plurality of injections and (ii) at least a second thermal dilution sensor.

2. The method of claim 1, wherein compensating for an injectate induced cooling of a thermal dilution sensor includes calculating an inside cooling effect on the first thermal dilution sensor in response to at least two introductions of injectate into the conduit.

3. The method of claim 1, wherein employing a plurality of injections includes introducing a first injectate having a first volume and introducing a second injectate having a different second volume.

4. The method of claim 1, wherein employing a plurality of injections includes introducing a first injectate over a first time period and introducing a second injectate over a different second time period.

5. The method of claim 1, wherein employing at least a second thermal dilution sensor includes inducing a second thermal offset in the second thermal dilution sensor resulting from travel of the injectate through the catheter.

6. The method of claim 1, wherein employing at least a second thermal dilution sensor includes thermally exposing the second thermal dilution sensor to a fractional portion of injectate introduced into the conduit.

7. The method of claim 1, wherein employing at least a second thermal dilution sensor includes locating the second thermal dilution sensor relative to one of the injectate traveling through the catheter and a blood flow, to impart thermal conductivity properties different from the first thermal dilution sensor.

8. A method of determining a blood flow rate in a conduit, the method comprising:
   (a) sensing a blood parameter related to blood temperature;
   (b) passing an injectate through a lumen in a catheter, the passing injectate inducing a measurement offset in a blood parameter sensor; and
   (c) compensating for the measurement offset of the blood parameter sensor by an amount corresponding to one of measurements from a plurality of injections or measurements from a plurality of thermal sensors.

9. The method of claim 8, wherein compensating for the measurement offset includes measuring a blood parameter at two spaced apart locations.

10. The method of claim 8, wherein compensating for the measurement offset includes introducing a first injectate volume into the blood flow and introducing a different second injectate volume into the blood flow.

11. A method of thermodilution measurement of a blood flow rate in a conduit, the method comprising compensating for an injectate induced thermal variance of a thermal dilution sensor, the induced thermal variance resulting from an injectate flow through a catheter, the compensating including employing a plurality of different injections or employing a plurality of thermal sensors.

12. The method of claim 1, further comprising:
   (a) calculating the blood flow rate from a measured first dilution curve corresponding to a first injectate volume having a first injectate time and a first injectate temperature, and from a measured second dilution curve corresponding to a second injectate volume having a second injectate temperature and a second injectate time.

13. The method of claim 1, further comprising:
   (a) determining the blood flow rate in response to a temperature of the blood flow, a temperature of the injectate, a volume of the injectate, a dilution curve from a proximal thermal dilution sensor and a dilution curve from a distal thermal dilution sensor, wherein the first thermal dilution sensor is one of the proximal thermal dilution sensor and the distal thermal dilution sensor, and the second thermal dilution sensor is a remaining one of the proximal thermal dilution sensor and the distal thermal dilution sensor, and at least a portion of the injectate is introduced into the blood flow at a location between the proximal thermal dilution sensor and the distal thermal dilution sensor.

14. The method of claim 1, wherein employing at least a second thermal dilution sensor includes:
   (a) exposing the first thermal dilution sensor to a first thermal influence of the injectate flowing in an injectate lumen in the catheter and to a first thermal influence of the blood flow diluted by the injectate, and
   (b) exposing the second thermal dilution sensor to a different second thermal influence of one of the injectate flowing in the injectate lumen and the blood flow diluted by the injectate.

15. The method of claim 1, wherein employing at least a second thermal dilution sensor comprises:
   (a) passing a first portion of an injectate volume through a first introduction port in the catheter, to combine the first portion of the injectate with the blood flow thereby forming a first diluted flow;
   (b) thermally sensing the first diluted flow with the first thermal dilution sensor;
   (c) passing a balance of the injectate volume through at least a second introduction port to combine with the first diluted flow to form a second diluted flow; and
   (d) thermally sensing the second diluted flow with the second thermal dilution sensor.

16. The method of claim 1, further comprising:
   (a) determining the blood flow rate corresponding to a factor representing an amount of an injectate volume passing through a proximal introduction port in the catheter, a difference between a blood flow temperature and an injectate temperature, and a difference between an upstream dilution curve obtained upstream of the proximal introduction port and a downstream dilution curve obtained downstream of the proximal introduction port.

17. The method of claim 1, further comprising:
(a) determining the blood flow rate corresponding to a first dilution curve from the first thermal sensor having first thermal conductive properties, and a second dilution curve from the second thermal sensor having different second thermal conductive properties, and an injectate volume.

18. The method of claim 1, wherein employing a plurality of injections includes introducing a first injectate having a first temperature and introducing a second injectate having a different second temperature.

19. The method of claim 1, further comprising measuring one of a velocity of sound in the blood, an electrical impedance of the blood, an optical density of the blood and a density of the blood.

20. The method of claim 1, further comprising employing one of a thermistor, a thermocouple, an electrical impedance sensor, a sound velocity sensor, optical density sensor and a blood density sensor.

* * * * *